A United States Patent [19]

Roberts

[11] Patent Number: 5,652,334
[45] Date of Patent: Jul. 29, 1997

[54] METHOD FOR DESIGN OF SUBSTANCES THAT ENHANCE MEMORY AND IMPROVE THE QUALITY OF LIFE

[75] Inventor: Eugene Roberts, Monrovia, Calif.

[73] Assignee: City of Hope, Duarte, Calif.

[21] Appl. No.: 117,927

[22] Filed: Sep. 8, 1993

[51] Int. Cl.⁶ .............................. A61K 38/00; C07K 5/10
[52] U.S. Cl. ............................................................ 530/330
[58] Field of Search .............................. 530/330; 514/18

[56] References Cited

PUBLICATIONS

Pabo et al, *Biochemistry*, 1986, 25, 5987–5991.
J. Scott Dixon, *Tihtech*, Oct. 1992 (vol. 10) pp. 357–363.

*Primary Examiner*—Cecilia Tsang
*Assistant Examiner*—S. G. Marshall
*Attorney, Agent, or Firm*—Rothwell, Figg, Ernst & Kurz

[57] ABSTRACT

Amnestic novel peptides are disclosed. A topographical map or surface which includes binding sites for peptides having amnestic procedures and the use of such surface to identify and synthesize such peptides is also disclosed.

1 Claim, 15 Drawing Sheets

METHOD FOR DESIGN OF SUBSTANCES THAT ENHANCE MEMORY AND IMPROVE THE QUALITY OF LIFE

FIELD OF THE INVENTION

This invention relates to memory enhancement and to improvement in the quality of life for human individuals who for various reasons including aging, disease, or injury show impairment of memory. More specifically, the invention relates to development of a topographic model on the basis of which it is possible to design and synthesize memory-enhancing and life-quality improving substances.

DEFINITIONS AND ABBREVIATIONS

β-A4=amyloid β protein
FAAT=footshock active avoidance training
ICV=intracerebroventricular
Ala=alanine
Cys=cysteine
Asp=aspartic acid
Glu=glutamic acid
Phe=phenylalanine
Gly=glycine
His=histidine
Ile=isoleucine
Lys=lysine
Leu=leucine
Met=methionine
Asn=asparagine
Pro=proline
Gln=glutamine
Arg=arginine
Ser=serine
Thr=threonine
Val=valine
Trp=tryptophan
Tyr=tyrosine

BACKGROUND OF THE INVENTION

Immediate post-training ICV administration of a synthetic peptide homologous to β-A4, [$Gln^{11}$]β-(1–28) [Asp Ala Glu Phe Arg His Asp Ser Gly Tyr Gln Val His His Gln Lys Leu Val Phe Phe Ala Glu Asp Val Gly Ser Asn Lys (SEQ ID NO: 1)] caused amnesia for FAAT in mice in dose-dependent fashion. Also amnestic were residues β-(12–28) [Val His His Gln Lys Leu Val Phe Phe Ala Glu Asp Val Gly Ser Ash Lys (SEQ ID NO: 2)], β-(18–28) [Val Phe Phe Ala Glu Asp Val Gly Ser Asn Lys (SEQ ID NO: 3)], and β-(12–20) [Val His His Gln Lys Leu Val Phe Phe (SEQ ID NO: 4)] (1). These amnestic peptides have in common the tripeptidic sequence Val Phe Phe (SEQ ID NO: 5). Residue β-(1–11) [Asp Ala Glu Phe Arg His Asp Ser Gly Tyr Gln (SEQ ID NO: 6)], which does not contain Val Phe Phe, was not amnestic (this study) FAAT experiments were performed with peptides containing the Val Phe Phe sequence from which was derived a topographic model for the binding site of amnestic peptides. Since the amnestic substances are memory-enhancing at lower concentration than those at which they cause amnesia, the model can be used to deduce the structure of potential memory-enhancing peptides and non-peptidic substances.

SUMMARY OF THE INVENTION

Structure-activity study with various peptides in memory-testing paradigms in mice has made possible generation of a topographic map for a hypothetical binding surface, Z, for amnestic peptides. On the model Z binding sites are distributed in clockwise rotation the following designated loci: (1) H-bonding; (2) aromatic; (3) cationic; (4) aromatic; and (5) anionic (FIG. 1, No. 1–3). Effects on retention of FAAT are rationalized in terms of fit to Z, making possible design of potential memory-modulating peptidic and non-peptidic substances. The similarity in brain function in various mammals, including human beings, as well as much previous experience in the field indicates that such substances will be effective memory-enhancers in men as well as mice. In no instance known to applicant has a model such as that above been suggested, nor have any of the memory-enhancing peptides described herein been suggested for use in improving memory.

Administration of such substances and their congeners orally, subcutaneously, intravenously, transcutaneously, intrathecally, sublingually, rectally, or intracisternally leads to a restoration of the balance between excitatory and inhibitory systems in the brain, a balance which is required for optimal acquisition and retention of learning. Their administration helps correct defects in this balance that arise, for example, as a result of aging, infections, and injury. Administration of such substances exerts recyberneticizing effects on nervous system function.

Another aspect of this invention comprises substances that have been designed to mimic the actions of the active peptides but which do not have the peptide structure and would not be subject to degradation of peptide-splitting enzymes in the gut or other tissues. Such organic chemical entities would have more prolonged desired effects at lower doses than the peptidic structures.

DESCRIPTION OF THE FIGURES

In FIG. 21B the conditions were such as to maximize retention of learning in vehicle controls.

EXEMPLIFICATION OF THE INVENTION

Materials and Methods

Figure 1:
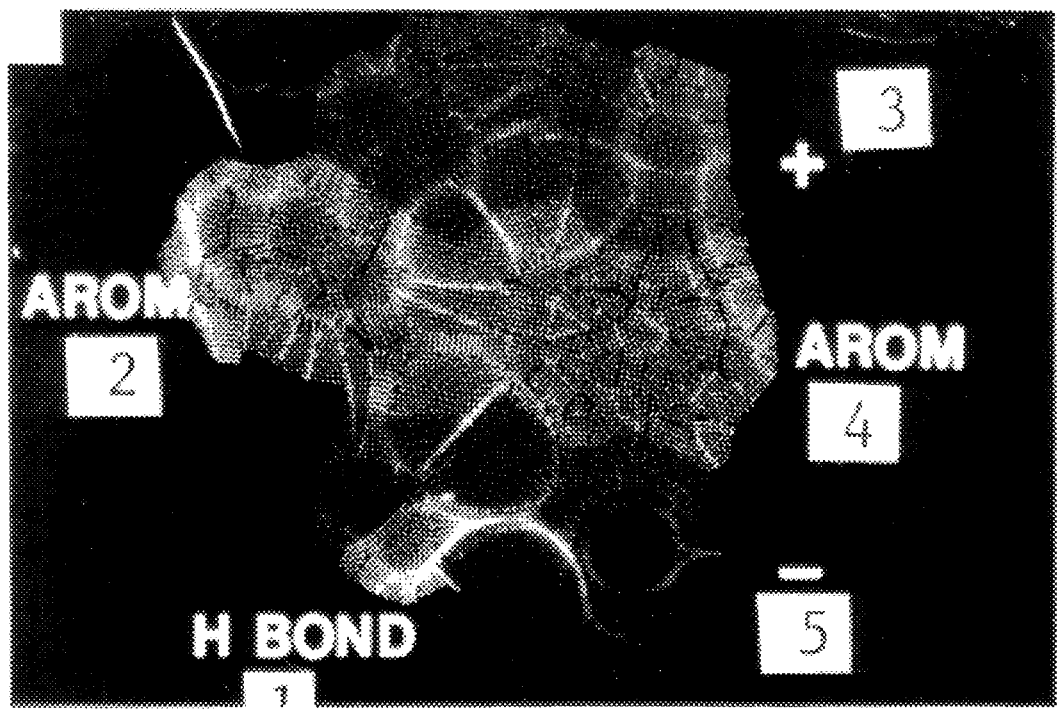
FIGS. 1–3 are computer generated models of a putative topographic site Z for the binding of amnestic peptides. Atoms are color coded as follows: carbon—gray; oxygen—red; nitrogen—blue; hydrogen—white.

Test Animals. After 1 week in the laboratory, CD-1 male mice obtained from Charles River Breeding Laboratories were caged individually 24–28 hours prior to training and remained singly housed until retention was tested one week later. Animal rooms were on a 12 hour light/dark cycle with lights going on at the hour of 0600. Median body weight was 35 g, with a range of 33–38 g. Mice were assigned randomly to groups of 15 in the experiments reported in FIGS. 1–18 and groups of 10 for the dose-response curves (FIGS. 19 and 20) and were trained and tested between the hours of 0700 and 1500.

Peptides Tested. With the exception of Val Phe and Phe Val from Sigma, all peptides used in these studies were synthesized and analyzed to establish purity by standard methods at the Beckman Research Institute. Peptides were dissolved in: (1) saline; (2) 8% vol/vol dimethyl sulfoxide; (3) glacial acetic acid neutralized with HCl; or (4) NaOH neutralized with HCl. Upon testing for retention of FAAT after receiving post-training ICV administration of 2 µl of the above vehicles, closely similar mean numbers of trials to criterion for the different vehicles were obtained: (1) 6.93±0.29; (2) 6.80±0.20; (3) 6.87±0.20; and (4) 6.53±0.22. Analysis of variance showing insignificant differences among the latter, the value for the most frequently employed (No. 2 above) was used for comparison with groups receiving test peptides.

With exception of dose-response curves, the experiments reported below tested whether or not there was an amnestic effect at 6.14 nmol of peptide per mouse. Although β-(1–18) was active at 1.5 nmol per mouse (1), the higher dose was chosen so that substances with weaker effects might be detected.

Apparatus, Training and Testing Procedures. The T-maze used for footshock active avoidance training (FAAT) consisted of a black plastic alley (46 cm long) with a start box at one end and two goal boxes (17.5 cm long) at the other. The start box was separated from the alley by a plastic guillotine door that prevented movement down the alley until training began. The alley was 12.5 cm deep and 9.8 cm wide. An electrifiable stainless steel rod floor ran throughout the maze.

Mice were not permitted to explore the maze before training. A block of training trials began when a mouse was placed in the start box. The guillotine door was raised and a muffled doorbell-type buzzer sounded simultaneously; footshock was 5 seconds later through a scrambled grid floor shocker (Colbourn Instruments, Model E13-08). The goal box first entered during the first set of trials was designated as "incorrect", and footshock was continued until the mouse entered the other goal box, which in all subsequent trials was designated "correct" for the particular mouse. At the end of each group of trials, the mouse was removed to its home cage.

As training proceeded, a mouse made one of two types of responses. A response latency longer than 5 seconds was classed as an escape from the footshock. A response latency less than or equal to 5 seconds was considered an avoidance, since the mouse avoided receiving a footshock. Two exclusion criteria were applied to reduce learning variability among mice, as follows. On the first training trials, mice with escape latencies greater than 20 seconds were discarded. Mice not having at least one errorless escape latency between 1.5 and 3.5 seconds on training trials 3 or 4 were excluded. The total exclusions were fewer than 15%. Mice received five such training trials. One week after training and post-trial administration of vehicle alone or vehicle containing test substance, T-maze training was resumed until each mouse made five avoidance responses in six consecutive training trials (trials to criterion). The recall score was taken to be the percentage of tested mice remembering original training.

Well-trained animals (recall score approximately 80%) were used to determine whether or not administered substances could cause amnesia. In these instances, training was performed under conditions that tend to maximize learning (sound intensity, 65 decibels; footshock current, 0.35 mA; intertrial interval, 45 seconds). In the cases in which it was desired to detect whether or not there was an enhancing effect on memory, training conditions were adjusted so that the initial recall score in vehicle controls was only approximately 20% (sound intensity, 55 decibels; footshock current, 0.30 mA; intertrial interval, 30 seconds).

Surgical Procedure in Preparation for Intracerebroventricular (ICV) Administration of Substances. ICV injection was the mode of administration of test substances because this eliminates problems of differential penetration of the blood-brain barrier. The following procedure was performed 24–48 hours prior to training. A single hole was drilled through the skull over the third ventricle (−0.5 mm relative to bregma, 0.5 mm right of central suture) while the mouse, appropriately anesthetized with methoxyflurane, was held in a stereotaxic instrument. The third ventricle was chosen as site of ICV drug injection because only a single injection is required and the drug quickly reaches limbic system structures, believed to be associated with memorial processes. Immediately after training, mice were anesthetized with enflurane, a short acting anesthetic, and given an ICV injection of 2 µl of vehicle alone or test substance in vehicle delivered over a 30-second period through a 31-gauge needle attached to a 10- µl syringe; the injection was given within 2–3 minutes after the training. Accuracy of injection was determined to be greater than 95% by due injection, monitored regularly.

Statistical Treatment of Data. All of the results are expressed in terms of the mean and standard errors of the mean (SEM). Significance of overall effects of treatment was determined by one-way analysis of variance (ANOVA) run on trials to criterion. Dunnett's t-test was used to make multiple comparison of individual test groups with control groups. See Bruning, J. E., et al., in *Computational Handbook of Statistics*, 2d ed., Scott, Foreman and Co., Glenview, pp. 18–30, 122–124, 128–130 (1977). Statistical comparison among experimental groups were made by Bukey's t-test. See Winer, B. J., *Statistical Principles in Experimentation Design*, 2d ed., McGraw-Hill, New York, pp. 196–210, 397–402 (1971).

RESULTS

Topography of a binding site deduced from structure-activity study of amnestic effects. Structural examination of CPK models of the peptides tested and superimposition of appropriate configurations of the active ones led to devisal of a 2-dimensional model of the site to which all of the amnestic substances might bind. Subsequently, the 3-dimensional binding surface "Z" for the peptides of this invention was generated by surrounding with small molecules that mimic the properties of amino acid side chains a peptide, Gln-Phe-Phe-γ-Aminobutyric acid SEQ ID NO:20 that fits well to all of the proposed contact points on the 2-dimensional map. A solvent-accessible surface was generated using the algorithm of Connolly (2). Peptides then were docked onto the surface and energy minimized to optimize contacts (Dreiding II forcefield (3)). Images were created with the program BIOGRAF (Molecular Simulations Waltham, Mass.). The topographic receptor map was energy-minimized to optimize contacts (Dreiding II forcefield (3)). Images were created with the program BIOGRAF (Molecular Simulations Waltham, Mass.). FIG. 1 depicts the topographic receptor map Z thus generated to facilitate discernment of those structural features of the peptides that correlate with effects of memory retention. The Dreiding structural representation permits much better visualization of the superimposition of the peptides on Z than do space-filling CPK models.

Figure 2:
Figure 3:
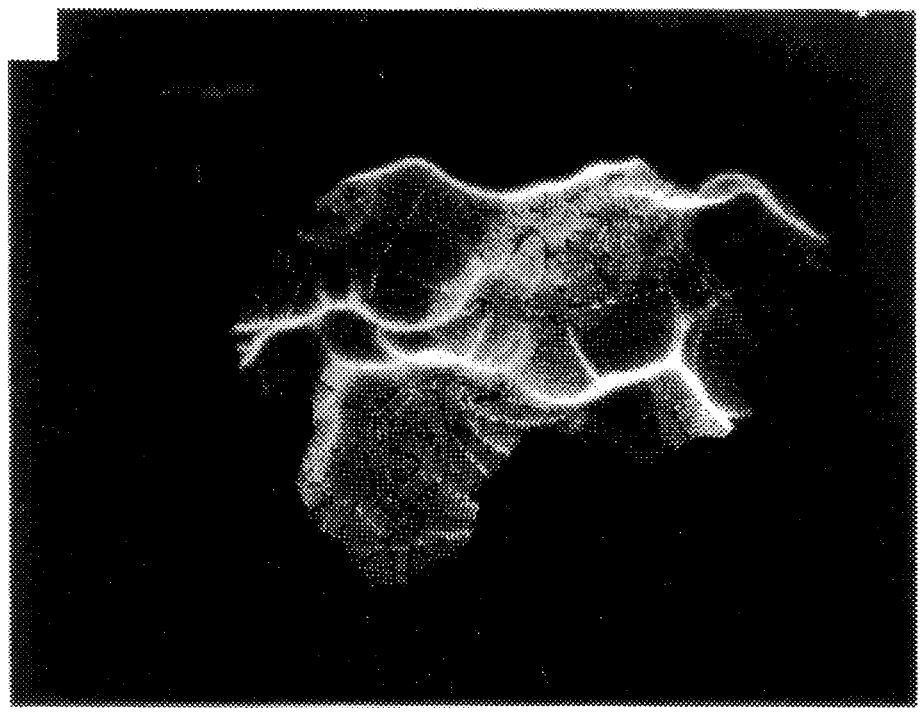
Figure 4:
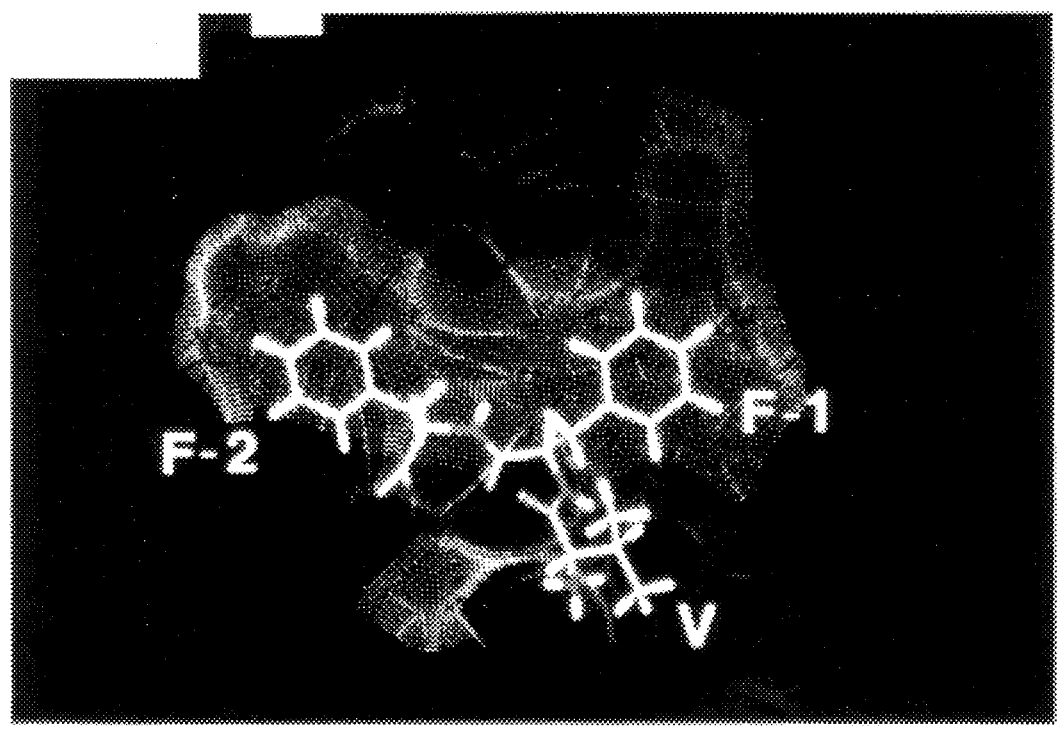
FIGS. 4–18 illustrate the fit of various peptides to the topographic site Z of FIG. 1.
Figure 5:
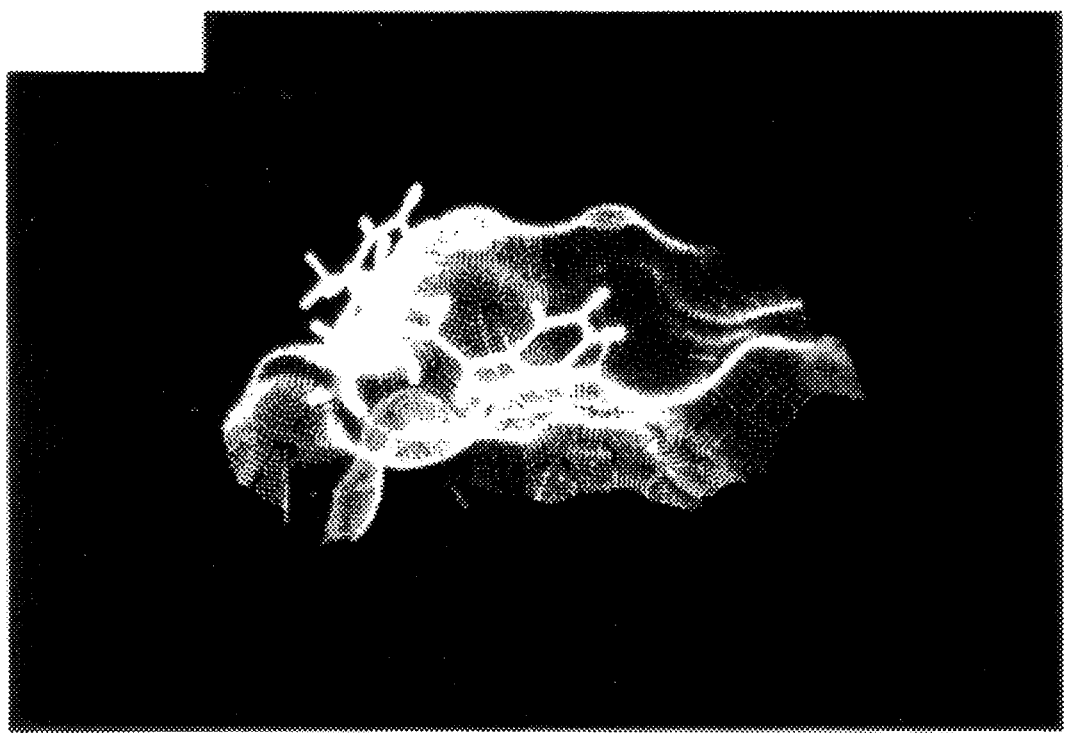
Figure 6:
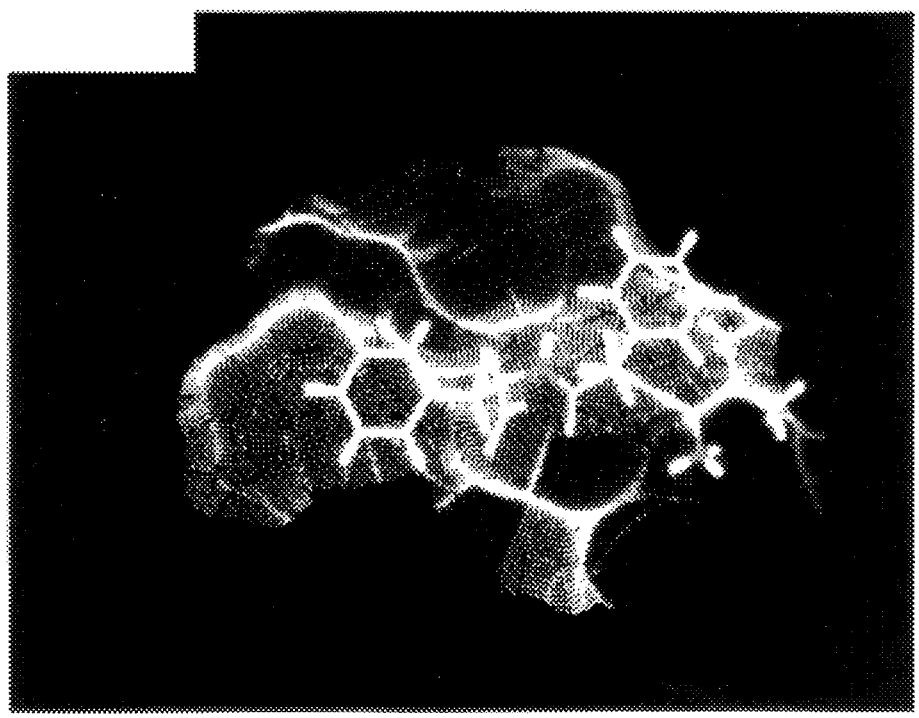
Figure 7:
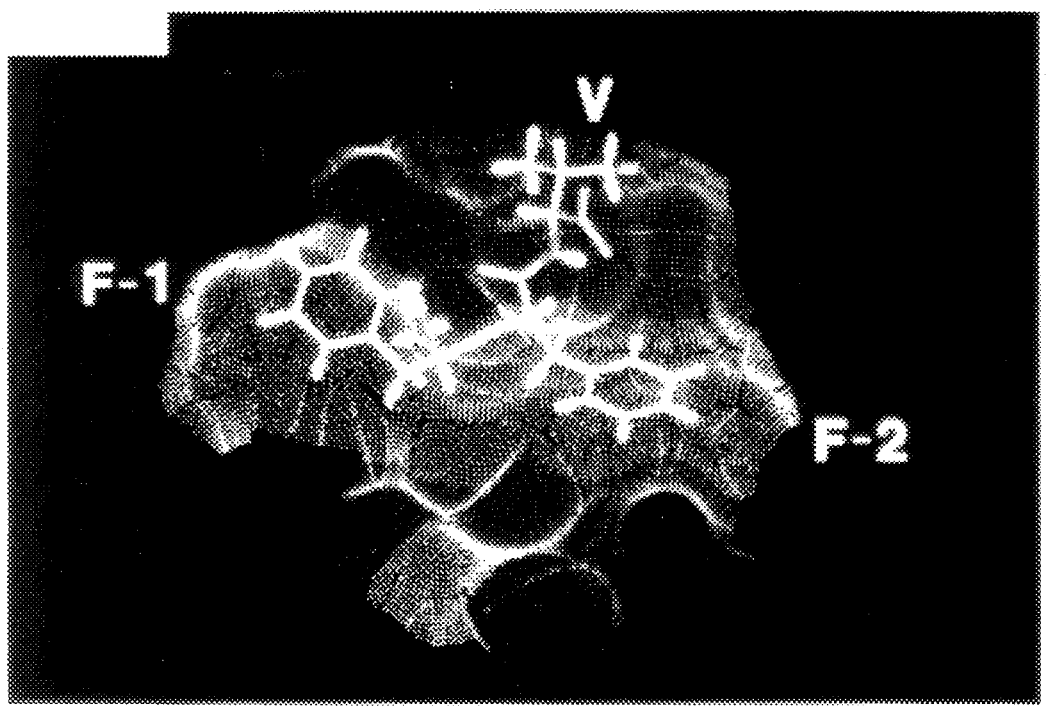
Figure 8:
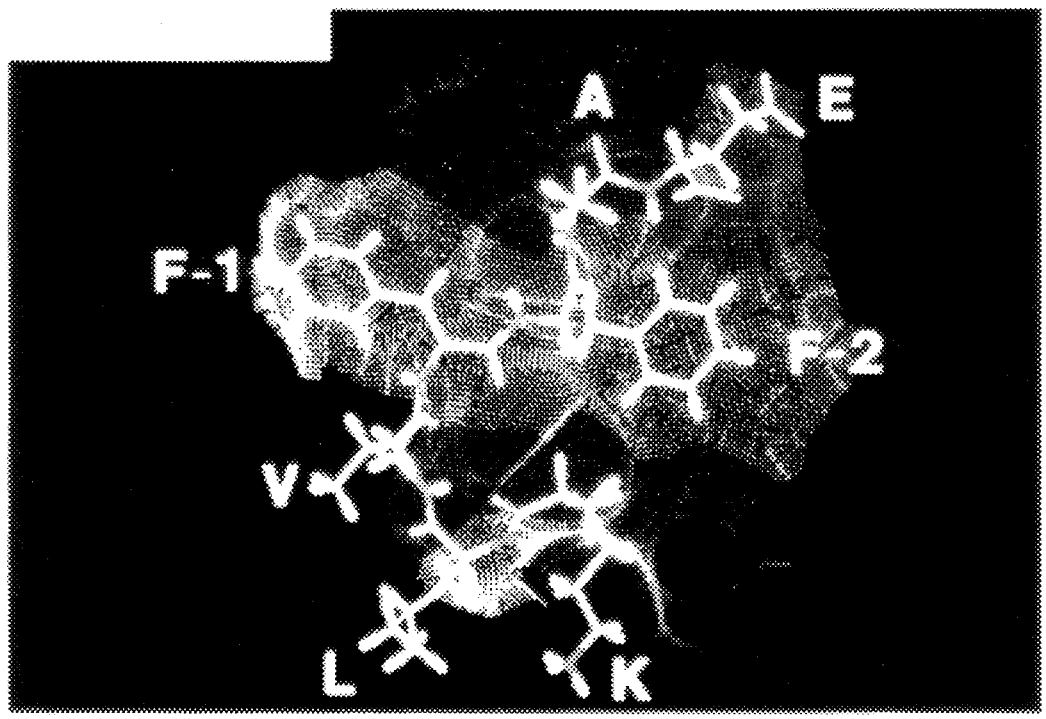
Figure 9:
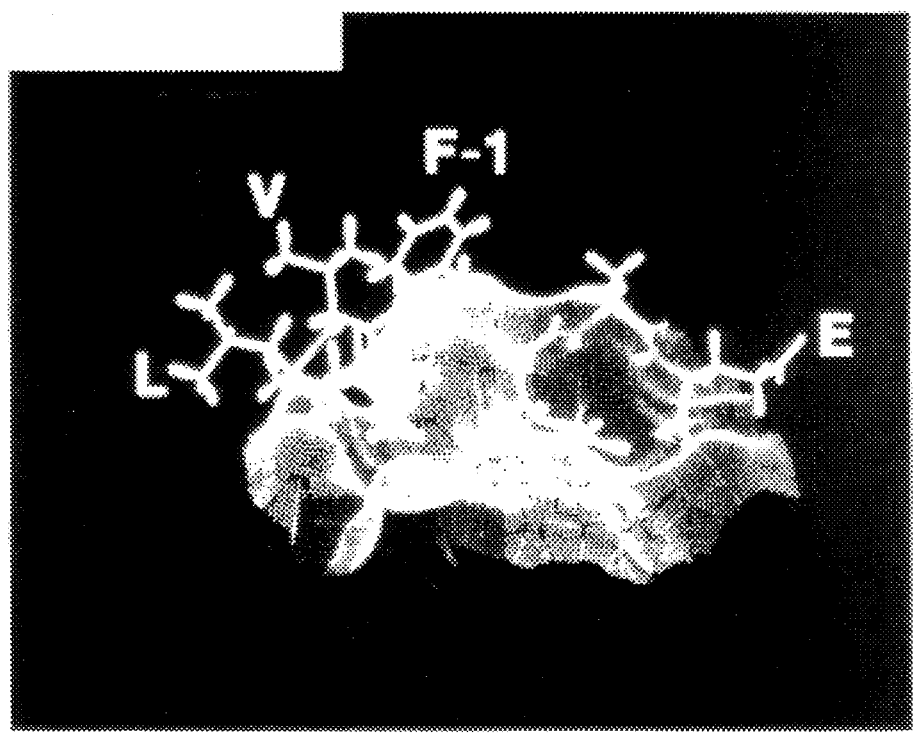

Numbering clockwise from the bottom left on FIG. 1, No. 1, the postulated sites on Z are characterized as (1) H-bonding; (2) aromatic; (3) cationic; (4) aromatic; and (5) anionic. Three views of the proposed surface of Z are shown (FIGS. 1–3). FIGS. 4 through 18 illustrate the fit to Z of relevant peptides in order of their discussion in this specification.

Attachment of Val Phe Phe to Z (FIGS. 4–6) is presumed to take place by interaction of the α-amino group of the N-terminal Val with anionic site 5 and, by association of the Phe-1 and Phe-2 residues with aromatic sites 4 and 2, respectively. The designations Phe-1 and Phe-2 are given to the Phe residues in a particular peptide in the order of the occurrence from the N-terminus.

There are five potential H-bonding sites on the side-chains of Val Phe Phe, one each on the two oxygen atoms of the C-terminal carboxyl group and three on the N-terminal amino group, for a total of five groups per molecule that may readily H-bond with water. Bound water molecules, in turn, may form H-bonds with other water molecules, in this manner organizing water clusters the sizes and shapes of which around the H-bonding groups are determined by combinatorial influences of molecular and environmental factors. Unbound Z site is presumed to have water clusters associated with sites 1, 3 and 5 (FIG. 1). Val Phe Phe (FIG. 4) is posited to orient on Z in such a manner that the attractive energy between Val Phe Phe and Z becomes great enough to squeeze out intervening water, in this way minimizing the energy of the system. In other words, the attractive forces between Z and Val Phe Phe are sufficiently greater than those of either one of them for water that they associate preferentially with each other, releasing bound water in the process.

Figure 20A:
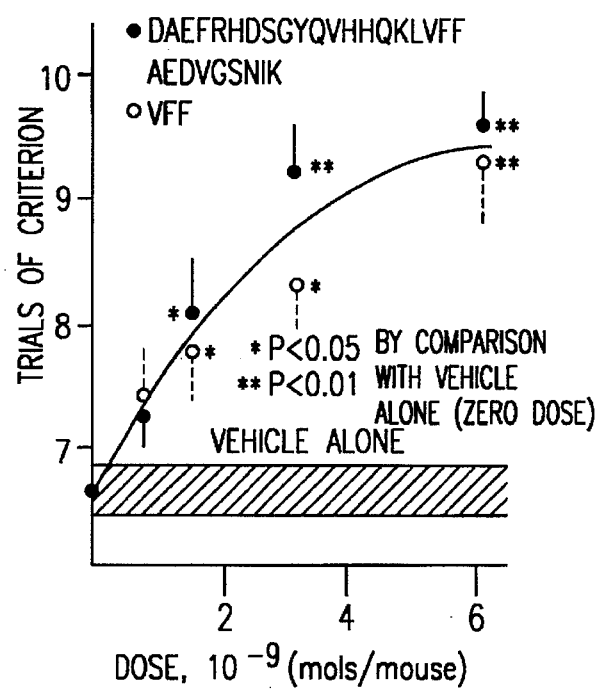
FIGS. 20A–20D depicts the dose-response curves comparing amnestic effects of Val Phe Phe with those of the β-A4 homologue [$Gln^{11}$]β-(1–28) (SEQ ID NO:1) (FIG. 20A) and amnestic effects of Ala Val Phe Thr (SEQ ID NO: 7) with those of Val Ile Pro (SEQ ID NO: 8) (FIG. 20B). The data for curves for [$Gln^{11}$]β-(1–28) (SEQ ID NO:1) and Val Ile Pro (SEQ ID NO:8) were taken from references 1 and 12, respectively. The dose-response curve for Lys Leu Phe Phe Val Ala Glu (SEQ ID NO: 9) is shown in FIG. 20C. Dose-response curves for Val Phe Phe (SEQ ID NO:5), Ala Val Phe Thr, and Lys Leu Phe Phe Val Ala Glu (SEQ ID NO:9) are compared with each other in FIG. 20D.
Figure 20B:
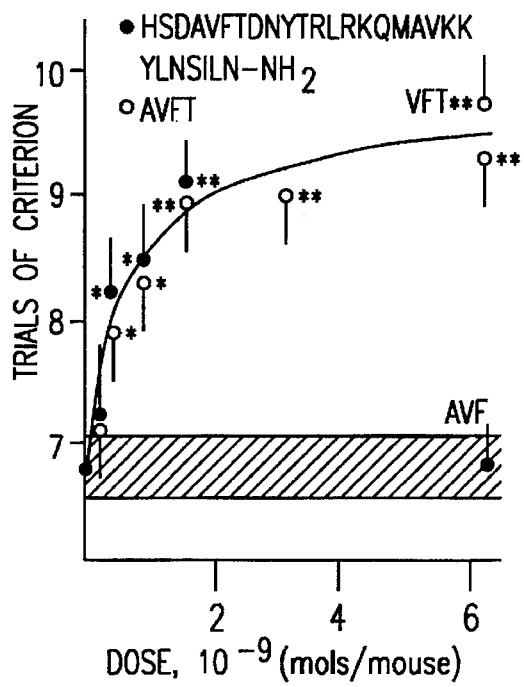

The molar amnestic efficacy of Val Phe Phe was not significantly different from that of the β-A4 homologue [Gln$^{11}$]β-(1–28) (FIG. 20A). If binding of its Val Phe Phe segment to Z is key to the amnestic effect of the latter, the flanking regions must contribute to strength of attachment since neither the α-amino group of V nor the carboxyl group of Phe-2 is available to contribute to binding efficacy.

If residues with H-bonding side-chains that do not bind to Z are added at either end of a peptide that, by itself, binds to Z, water clusters on the non-binding moieties may become sufficiently large and stable so that resulting physical and energetic barriers deter effective attachment of the peptide to Z. A curvilinearly decremental trend in amnestic potency was noted with increasing numbers of side-chain H-bonding groups in such peptides related to Val Phe Phe (FIG. 19, curve A).

Phe Phe Val, which also is amnestic (FIG. 19, curve B) shares aromatic sites 2 and 4 on Z with Val Phe Phe, but the C-terminal carboxyl group of Val in Phe Phe Val is directed to cationic site 3 (FIG. 1, No. 7). Addition of binding-irrelevant, H-bonding groups to Phe Phe Val also reduced amnestic potency (FIG. 19, curve B). It is presumed that a water cluster can be mobilized on the amide nitrogen of a peptide bond when Gly is the C-terminal residue in the peptide because, uniquely among the amino acids, C-terminal Gly offers no side-chain interference to water cluster formation. For the latter reason, the number of H-bonding groups assigned to a peptide was increased by one in the case of peptides with a C-terminal Gly (FIG. 2B; Phe Phe Val Gly (SEQ ID NO:11) and Asp Phe Phe Val Gly).

Lys Leu Val Phe Phe Ala Glu (SEQ ID NO: 13), which comprises residues 16–22 of β-A4, was not amnestic (FIG. 19, curve A), while the inversion of Val Phe Phe to give Lys Leu Phe Phe Val Ala Glu (SEQ ID NO:9) resulted in an amnestic peptide (FIG. 2, upper right; FIG. 20C). Lys Leu Val Phe Phe Ala Glu (SEQ ID NO: 13) fits site Z well, making 5-point attachment in the following manner (FIG. 10): site 1, α-amino group of Lys; site 2, Phe-1; site 3, α-carboxyl group of Glu; site 4, Phe-2; site 5, ε-amino group of Lys. If the Phe-1 and Phe-2 residues of SEQ ID NO: 13 are arranged so as to fit sites 2 and 4, respectively, the α-carboxyl group of Glu could interact coulombically with cationic site 3 (FIG. 1, Nos. 8 and 9); but the unrealistic energetic demand of the naked aqueous exposure of the hydrophobic Leu Val Phe segment that arises in this configuration (FIGS. 8 and 9) would preclude the existence of such a conformation of the peptide in this instance and, therefore, its binding to Z.

Figure 19:
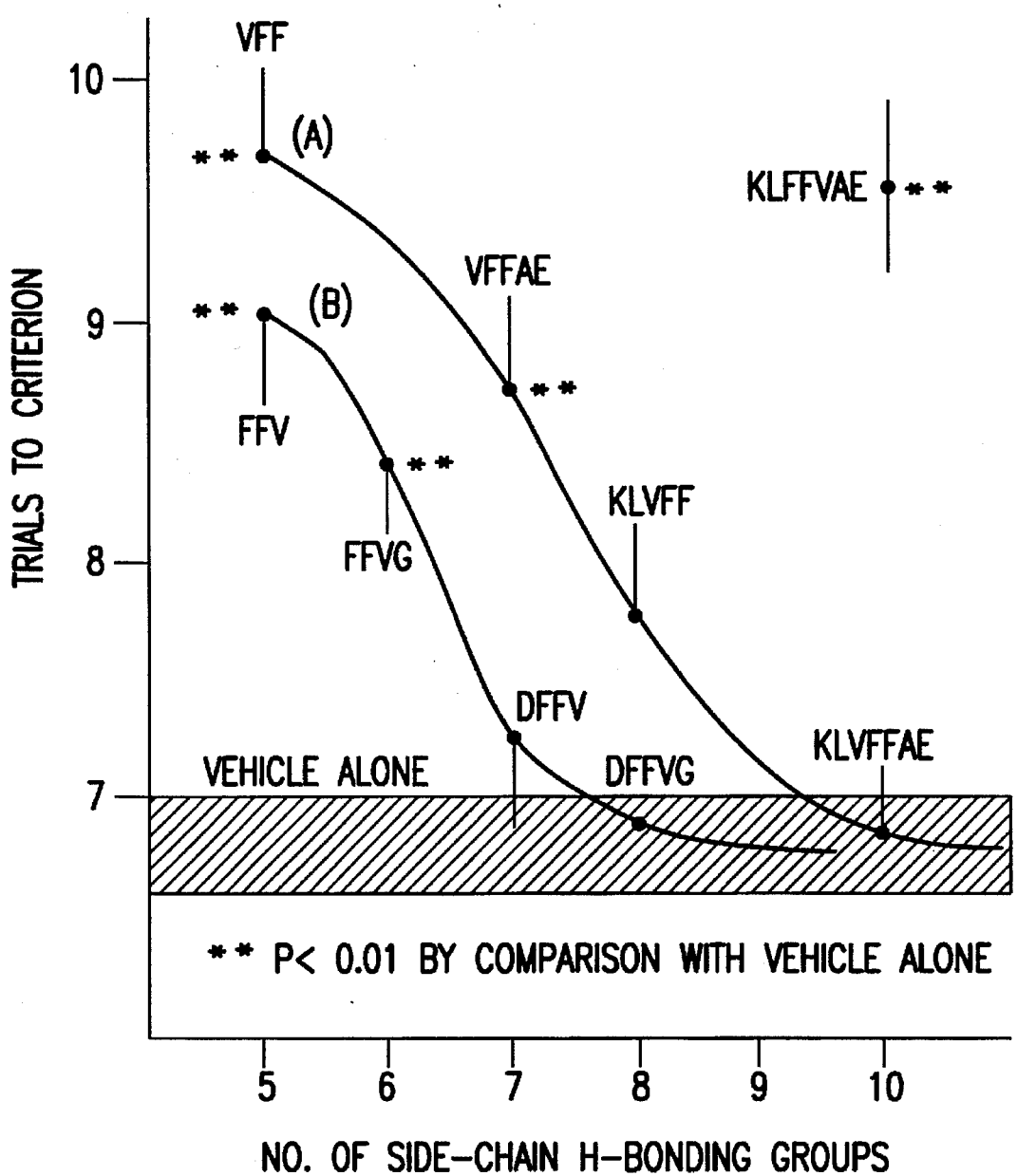
FIG. 19 depicts the decrease of amnestic potency of peptides as a function of H-bonding capacity. The special role of C-terminal G is discussed in the text.
Figure 20C:
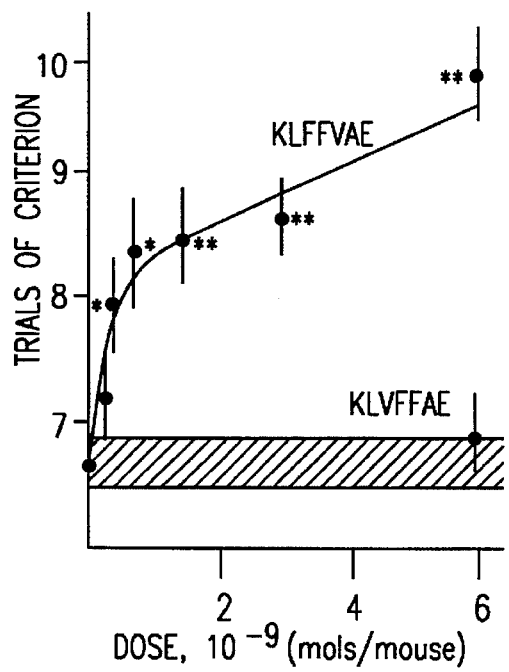
Figure 20D:
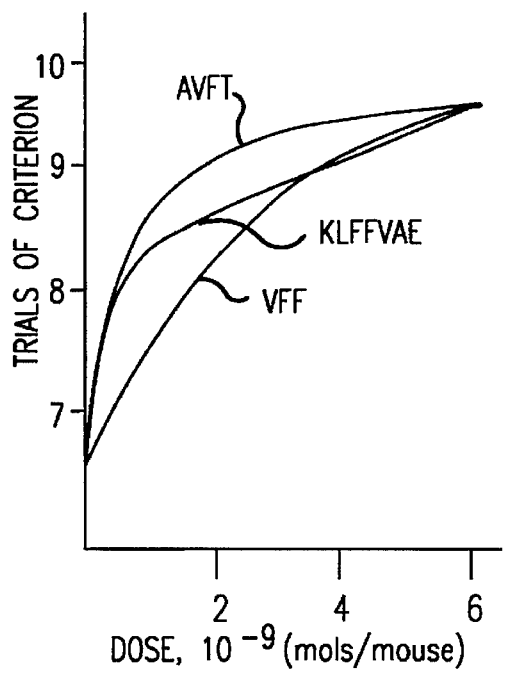

Although SEQ ID NO: 13 is not amnestic, Val Phe Phe Ala Glu is amnestic (FIG. 19, curve A). The latter peptide attaches in the following manner (figure not shown): site 5, α-amino group of Val; site 4, Phe-1; site 2, Phe-2; and site 3, α-carboxyl group of Glu. The lesser potency of Val Phe Phe Ala Glu than that of Val Phe Phe may be attributable to the greater energy required for desolvation of Val Phe Phe Ala Glu to take place (FIG. 19, curve A).

Peptide β-(1–11) (SEQ ID NO:6), which does not have a Val Phe Phe sequence, is not amnestic (trials to criterion 6.93±0.28 compared to 6.80±0.21 for vehicle controls). Assuming that β-A4 binds to the site that Z was designed to represent, the latter and other observation suggest the possibility that β-A4 and some of its larger amnestic fragments, e.g., β-(12–28) (SEQ ID NO:2), may require for attachment on a small segment that includes the Val Phe Phe sequence or a portion thereof. That even a small peptidic segment of a large protein molecule may have great functional significance is illustrated by the fact that the tripeptide, Arg Gly Asp (SEQ ID NO: 14), is integral to the cell attachment site of fibronectin and may be involved in cell attachment-promoting activity of collagen as well as of a variety of other proteins of great functional importance (4). In this regard, it is of interest that single or multiple Val Phe Phe sequences exist in approximately 3% of the protein sequences in the Swiss-Prot data base. Among the Val Phe Phe-containing proteins are receptors for serotonin, acetylcholine, norepinephrine, γ-aminobutyric acid, glucocorticoids, androgens, progesterone, natriuretic peptide, insulin, and transferrin. Aberrant binding of β-A4 or related substances to Val Phe Phe biding sites on membranes may wreak havoc with cellular signal transduction. β-A4 and the larger amnestic fragments derived from it possibly may combine with Z in the form of aggregates rather than as monomers. Such peptides are known to self-associate, forming anti-parallel β-sheets of still undetermined structure (5–9). β-A4 also binds with high avidity to apolipoprotein Glu, with which it coexists in senile plaques; and this complex might bind to Z (10, 11). Both Phe residues in Val Phe Phe are not required to produce amnesia, since Val Phe (FIG. 1, No. 11) and Phe Val (FIG. 1, No. 12) also were amnestic. However, neither Phe Phe (FIG. 1, No. 13) nor Val Val (not shown) was amnestic (trials to criterion: vehicle, 6.80±0.21; Val Phe, 9.13±0.42, p<0.01; Phe Val, 0.4±0.46, p<0.01; Phe Phe, 7.0±0.42, ns; Val Val, 6.8±0.31, ns). Val Phe and Phe Val both fit well to portions of Z, their Phe groups binding to aromatic site 4, the free amino group of Val binding to anionic site 5 and the free carboxyl group of Val in Phe Val binding to cationic site 3.

Figure 13:
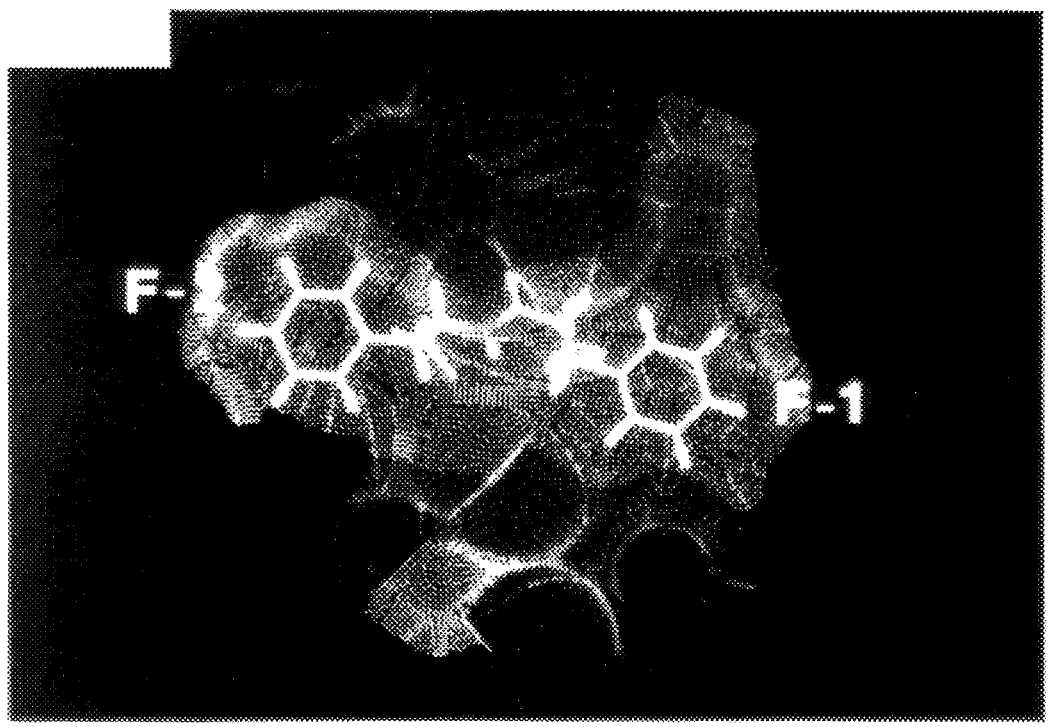
Figure 14:
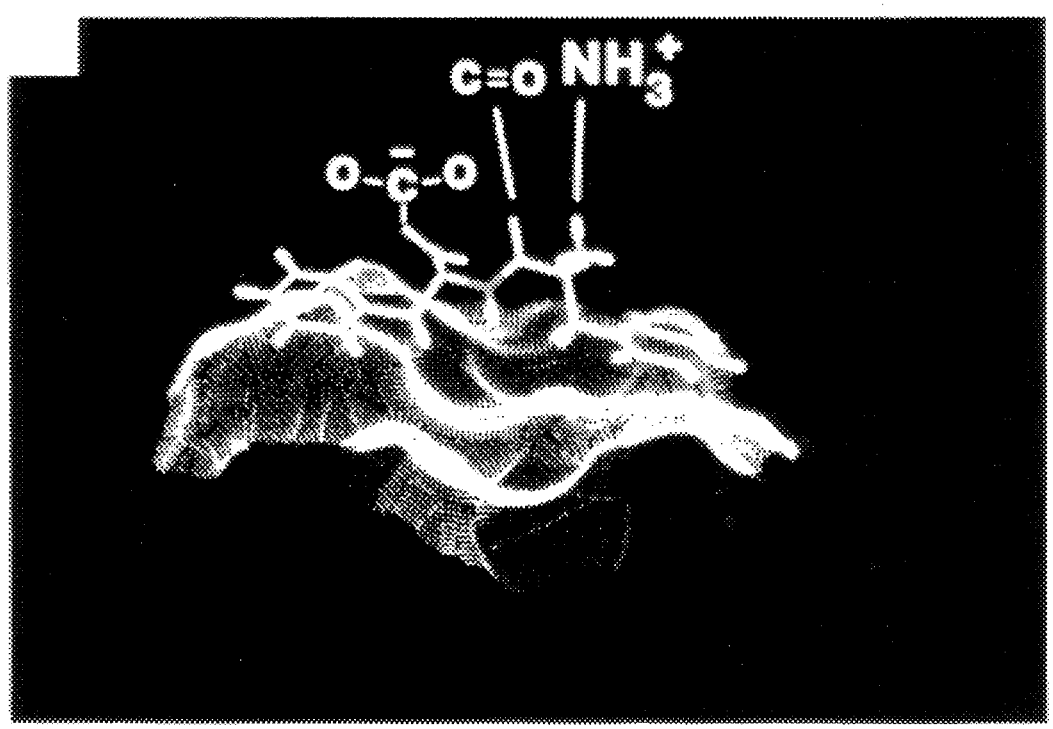
Figure 15:
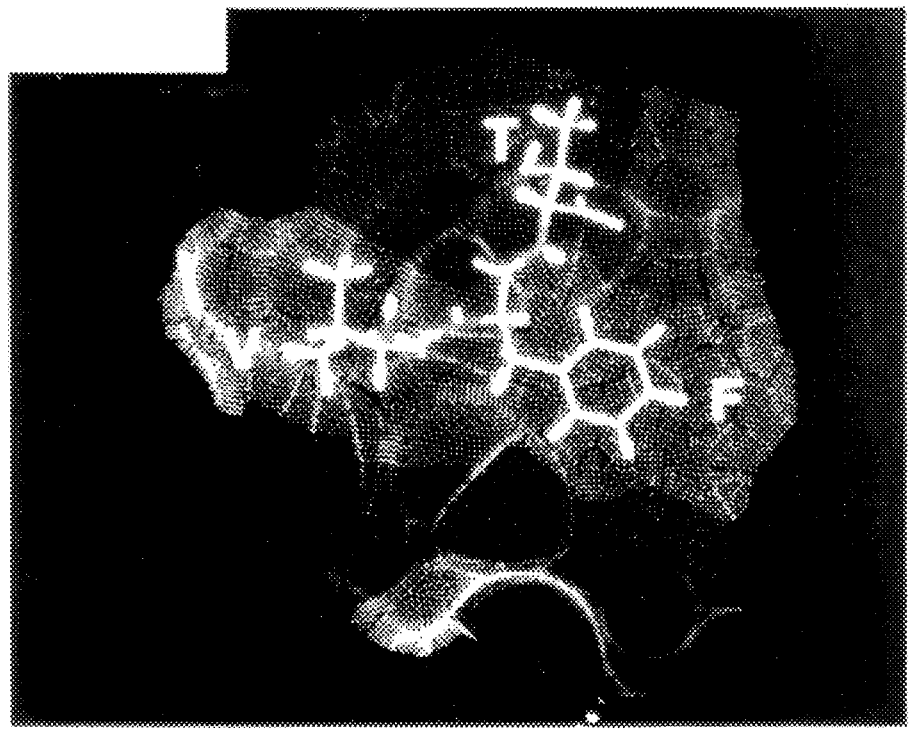
Figure 16:
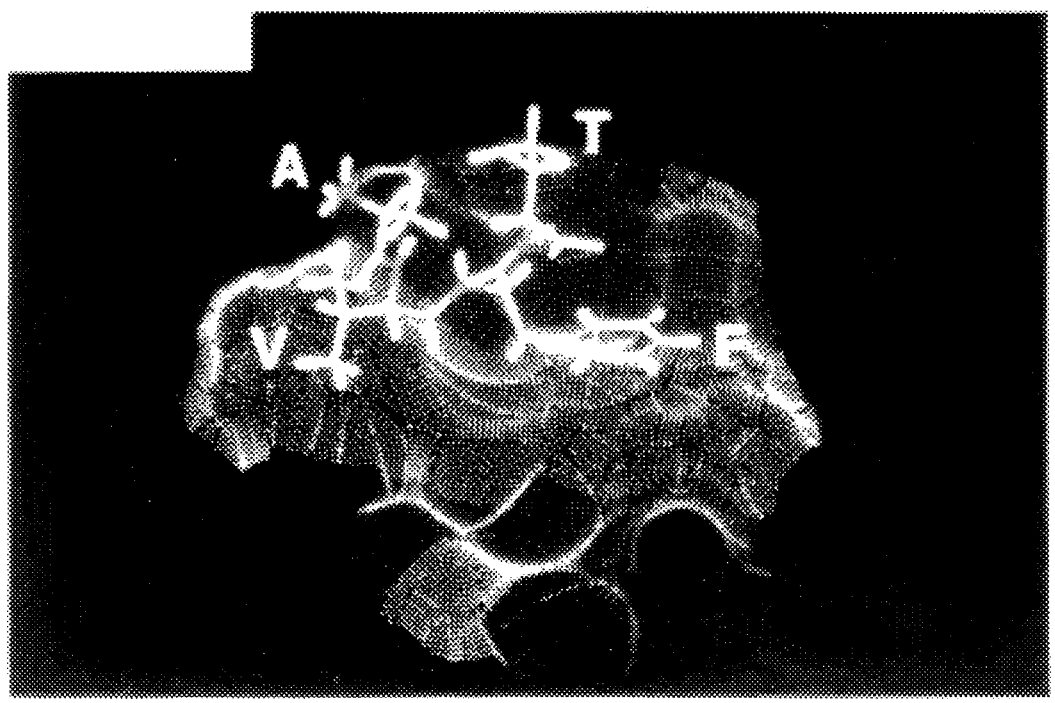
Figure 17:
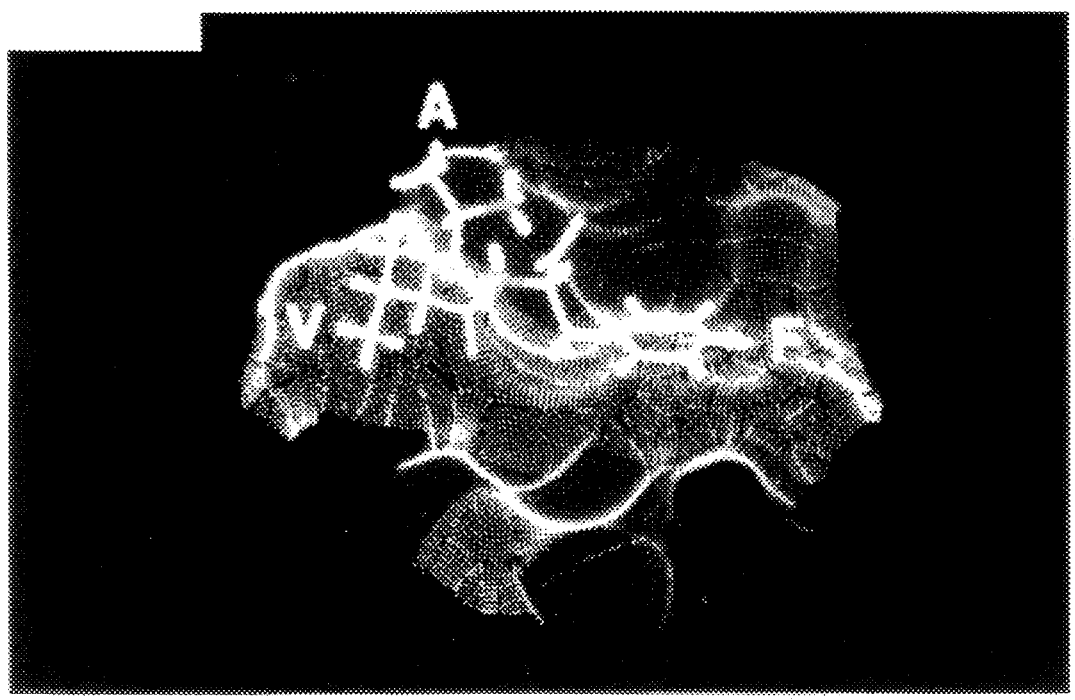

The best fit of Phe Phe to Z probably would occur if Phe-1 and Phe-2 were apposed to aromatic sites 4 and 2, respectively (FIGS. 13 and 14). However, this would require aqueous exposure of the closely grouped hydrophilic N-terminal amino group, the C-terminal carboxyl group, and the peptidic amide group. The energy required to remove resultant water clusters from Phe Phe for binding to take place in this form probably would be too great to permit its effective binding of Phe Phe to Z. If Val Val were oriented on Z in a manner similar to Val Phe, its affinity for Z would be less than that of Val Phe because the energy of binding of the C-terminal Val to aromatic site 4 would be considerably less than that of Phe. The probability of attachment of Val Val to the two aromatic sites of Z would be less even than that of Phe Phe.

Vasoactive intestinal peptide (VIP) (His Ser Asp Ala Val Phe Thr Asp Asn Tyr Thr Arg Leu Lys Gln Met Ala Val Lys Lys Tyr Leu Asn Ser Ile Leu Asn-NH$_2$ (SEQ ID NO: 15)) is amnestic in the FAAT paradigm (12). Ala Val Phe Thr (FIG. 16), comprising residues 4–7 (underscored above) of this 27-residue peptide, was amnestic with a molar efficacy similar to that of VIP (FIG. 3B). Val Phe Thr (residue 5–7) also was amnestic (FIG. 15; FIG. 3B), but Ala Val Phe (residue 4–6; FIG. 1, No. 17) was not (FIG. 3B). Val Phe Thr fits excellently to a portion of Z, with Val and Thr interacting coulombically with sites 5 and 3 through their respective free amino and free carboxy groups, with Phe associating with aromatic site 4. Although the Ala residue of Ala Val Phe Thr (FIG. 16) protrudes from the surface of Z into the aqueous medium, the disposition of the hydrophobic portions of Ala and Val is such as to tend to prevent formation of large water clusters around the closely lying hydrophilic groups. Ala Val Phe would bind to Z poorly, at best, because the most favorable binding sites for the uncharged internal Val residue and for the Phe would be aromatic sites 2 and 4, respectively, the affinity of Ala Val Phe for Z probably lying midway between that of Val Val and Phe Phe, which are amnestically ineffective (see above).

Figure 10:
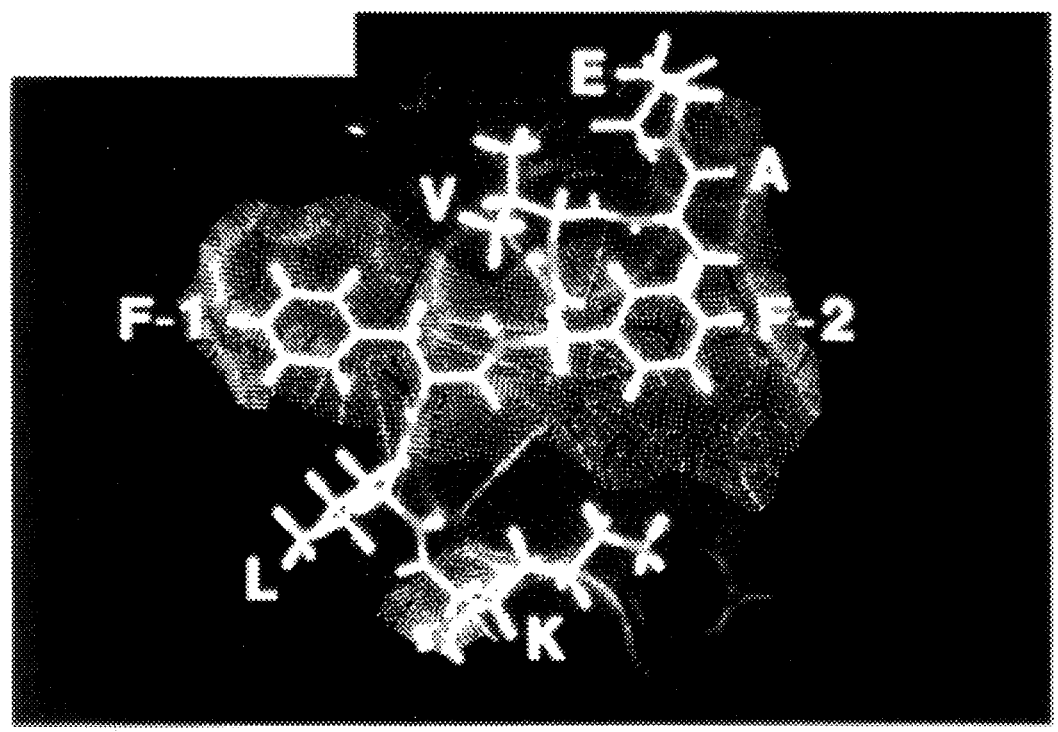
Figure 11:
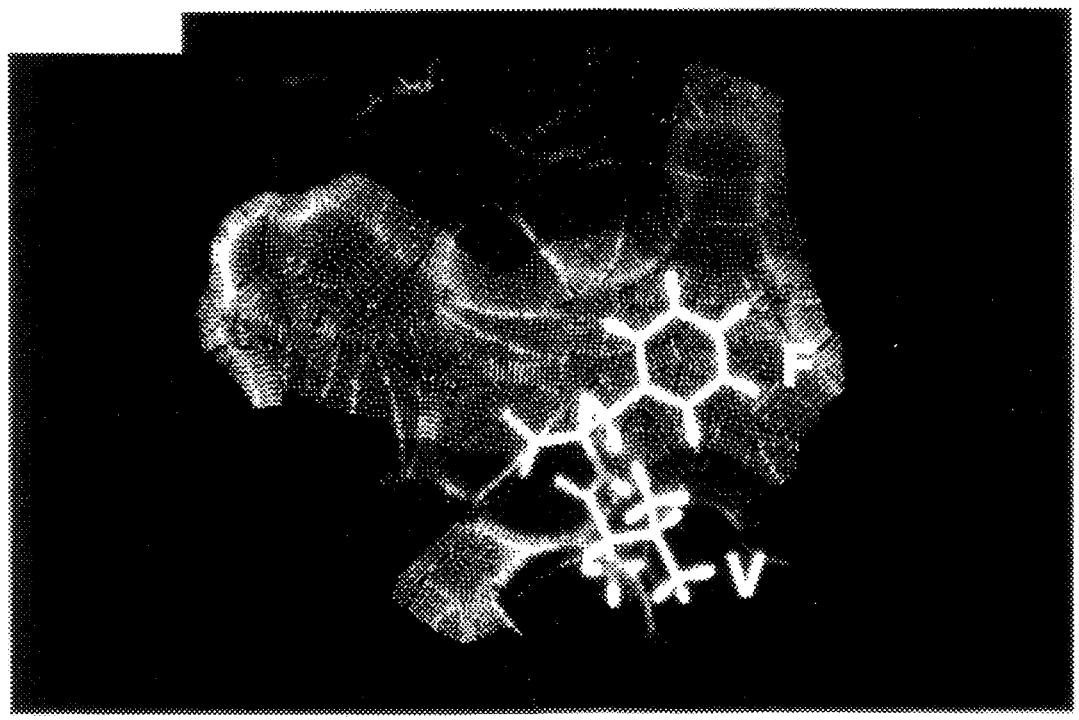
Figure 12:
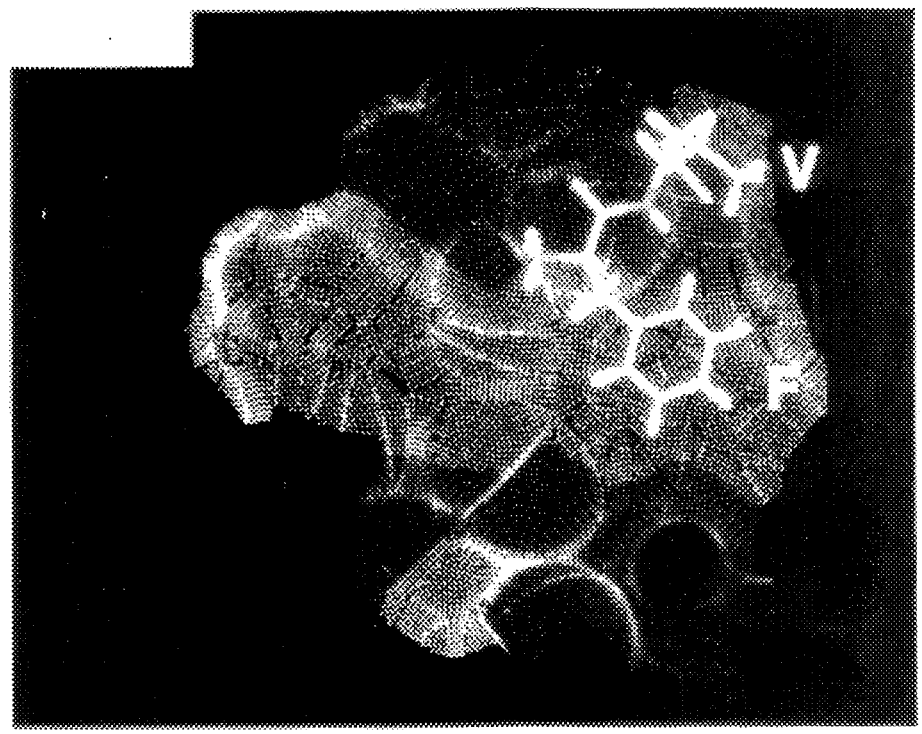

The 2-Dimensional Model. A 2-dimensional model of Z was constructed from consideration of data discussed in the preceding section and was influenced by the proposed 5-site interaction with Lys Leu Phe Phe Val Ala Glu (SEQ ID NO: 9) (FIG. 10). Every amnestic peptide tested up to that point contained a Val residue, and the small amnestic peptides were fragments of larger ones (β-A4 and VIP) that also were amnestic. It was recognized that credibility of the model would be enhanced if a Val-free amnestic fragment of a memory-enhancing peptide were to be found to fit the topography of Z.

A likely candidate for the later was the tetrapeptide Gln Phe Phe Gly (SEQ ID NO: 12) (underscored below) (FIG. 18) that comprises residues 6-9 of the 11 residue substance Pro (Pro Arg Pro Gly Pro Gln Gln Phe Phe Gly Leu Met-NH$_2$ (SEQ ID NO: 16)). Substance Pro has been reported to enhance memory retention (e.g., see references 13-16) and to counteract trophic and toxic effects of B-A4 on hippocampal neurons in culture (see reference 17). Gln Phe Phe Gly fits the original Z surface remarkably well at sites 1, 2, 4 and 5. The substitution of γ-aminobutyric acid for Gly at the C-terminus improved the fit to site 3, the latter substance (SEQ ID NO:20) being used to devise the current receptor map (FIGS. 1–3).

Figure 18:
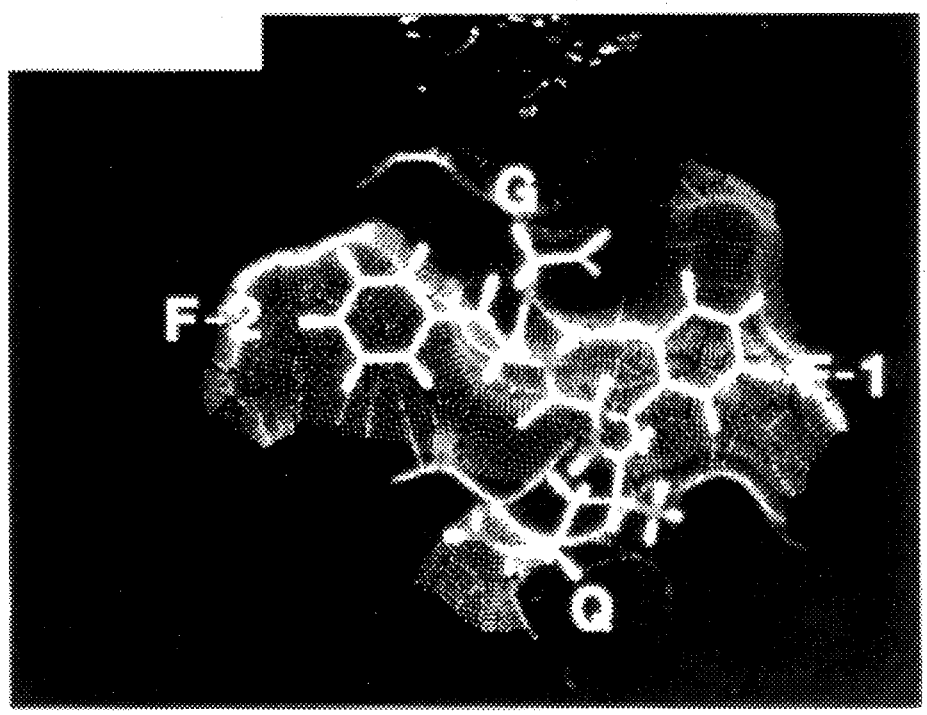

Referring to FIG. 18, the γ-amide group of the Gln residue of Gln Phe Phe Gly (SEQ ID NO: 12) H-bonds to site 1 and its α-amino group interacts electrostatically with site 5. Residues Phe-1 and Phe-2 associate with aromatic sites 4 and 2, respectively, and the carboxyl group of the C-terminal Gly falls just close enough to site 3 to engage in weak coulombic interaction with it. With γ-aminobutyric acid substituting for Gly, the terminal carboxyl group fits perfectly onto site 3.

The fact that Gln Phe Phe Gly (SEQ ID NO: 12), a Val-free fragment of the memory-enhancing substance Pro, is itself amnestic accords with the premise that Z defines the generally features of a binding site for amnestic substances. Structural requirements for binding to Z appear to be quite fastidious since some peptides similar to Gln Phe Phe Gly are not amnestic. The mean trials to criterion ±SEM and p values for comparison with vehicle are: vehicle alone, 6.80±0.21, Gln Phe Phe Gly, 0.0±0.46, p<0.01; Gln Phe Val Gly, 6.80±0.39, ns; Ser Phe Phe Gly, 7.33±0.46, ns; Ser Phe Val Gly 7.47±0.47, ns. The model Z is the basis for the devisal of memory-enhancing substances.

Dual effects usually are observed in studies of memory enhancement by exitatory substances (18). In the effective dose ranges, progressively increasing doses first increase response to a maximum, beyond which decreasing responses are observed, until a dose is reached at which no significant effects are seen over the controls. A copendium of results in the literature showed that this phenomenon was observed for 27 memory-enhancing compounds given by seven routes of administration to six different species of organisms in 15 laboratories (19).

Figure 22C:
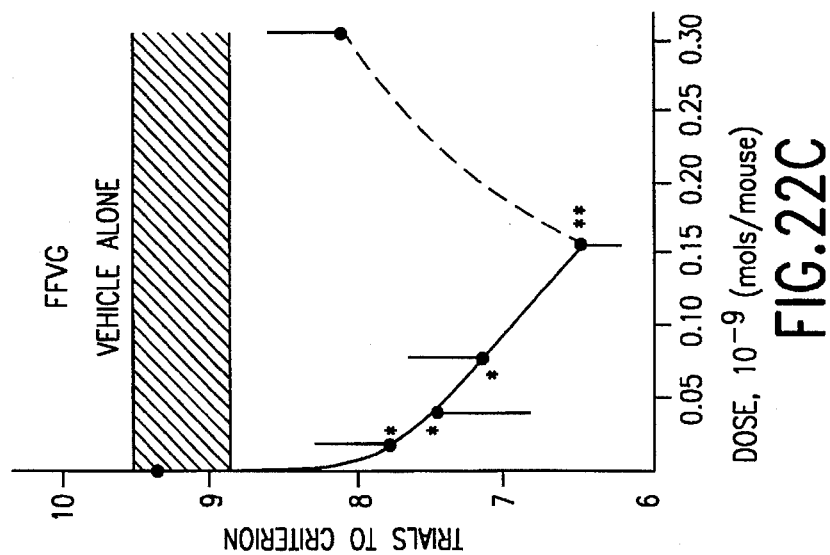
FIGS. 22A, 22B and 22C depict a comparison of memory-enhancing potencies of Val Phe Phe Val Val Phe (SEQ ID NO: 10), and Phe Phe Val Gly (SEQ ID NO: 11) from experiments performed to obtain poor retention in vehicle controls.
Figure 22B:
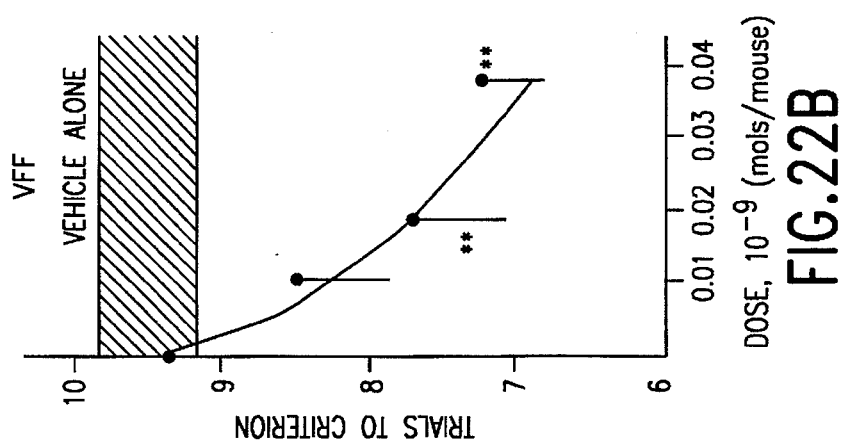
Figure 22A:
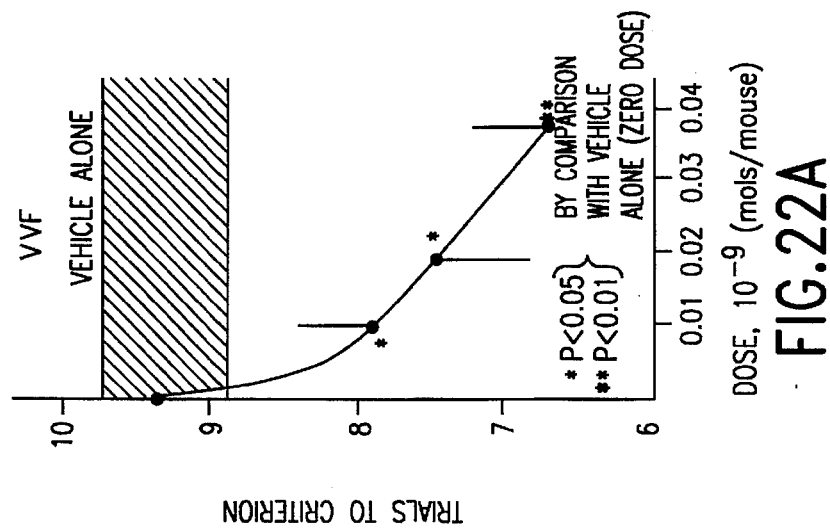
Figure 23A:
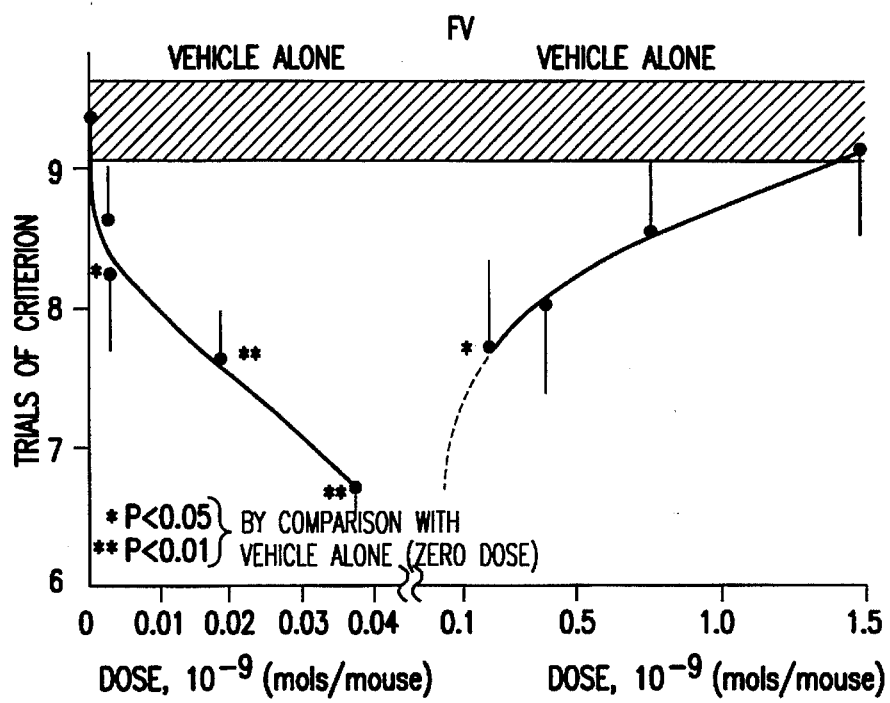
FIG. 23A and 23B depicts dose-dependence of memory-enhancing and amnestic effects of Phe Val under conditions of poor retention for controls. Comparison of effects of Val Phe (insert) with those of Phe Val in the memory-enhancing dose range.
Figure 23C:
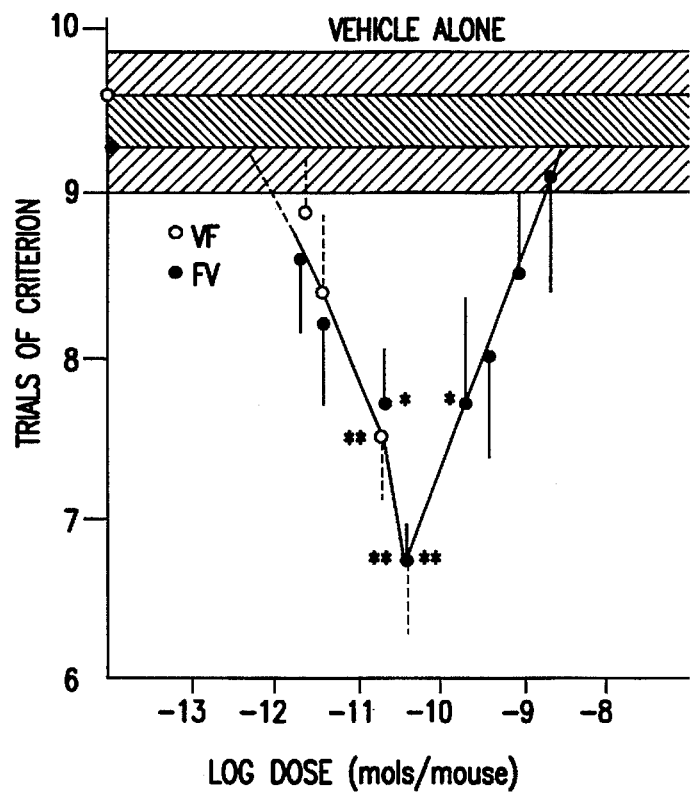
FIG. 23C depicts a log-dose plot of the same data as shown in FIG. 23A in order to facilitate comparison with date for Gln Phe Phe Gly (SEQ ID NO: 12) in FIG. 24.
Figure 23B:
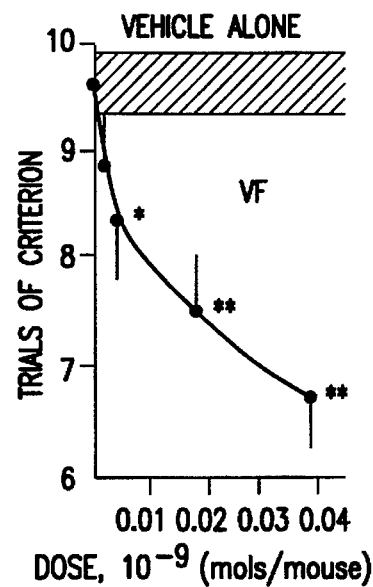
Figure 24:
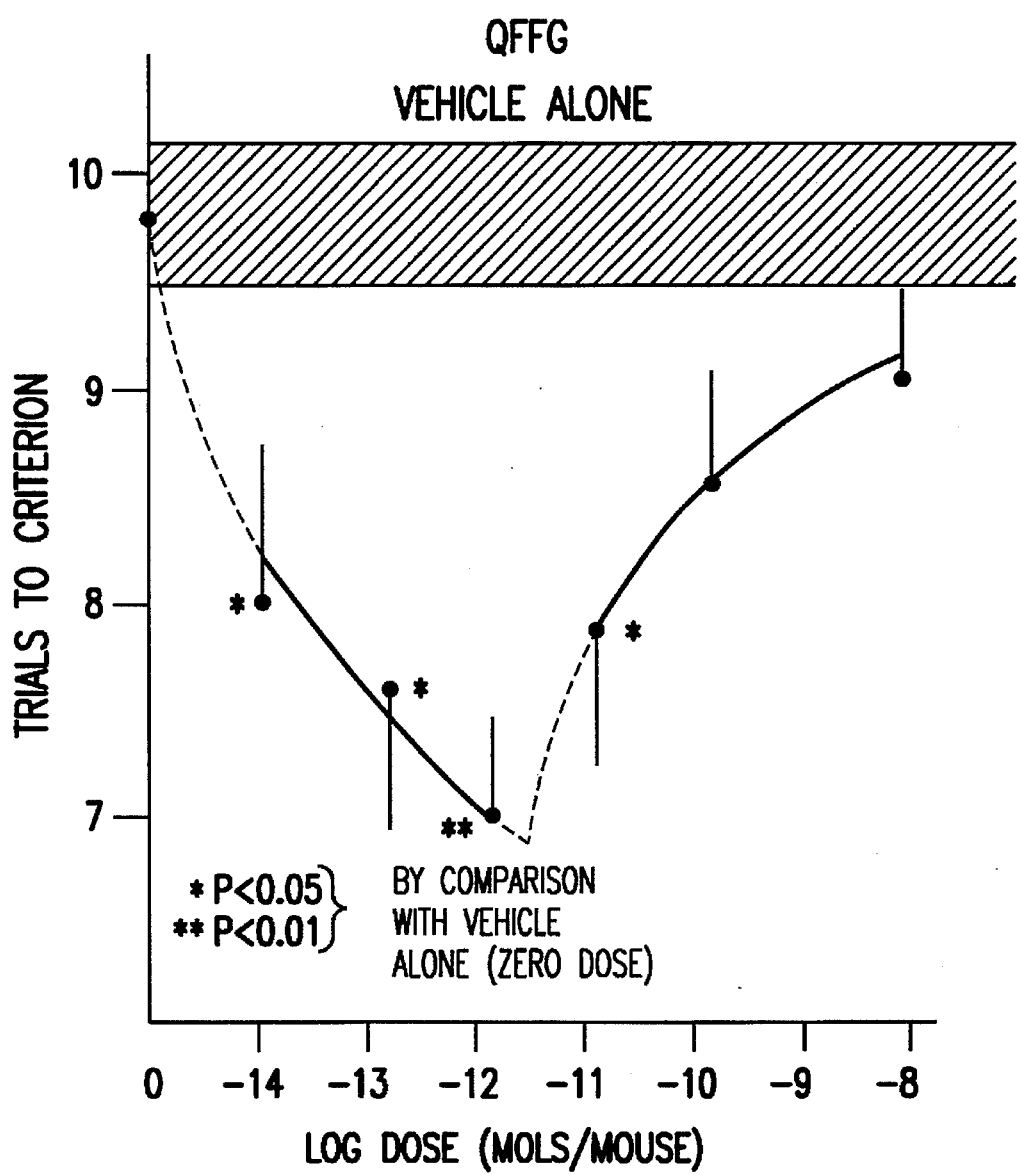
FIG. 24 depicts a log-dose plot of memory-enhancing and amnestic effects of SEQ ID NO: 12 in experiments with mice showing poor retention with vehicle alone.

The model Z was developed using an amnestic paradigm. Actually, six key substances used in the development of Z are memory-enhancers at far lower doses than those at which they show amnestic effects (FIGS. 22–24 and Table 1). The groups on Z with which these substances are presumed to combine are shown in Table 1.

Figure 21B:
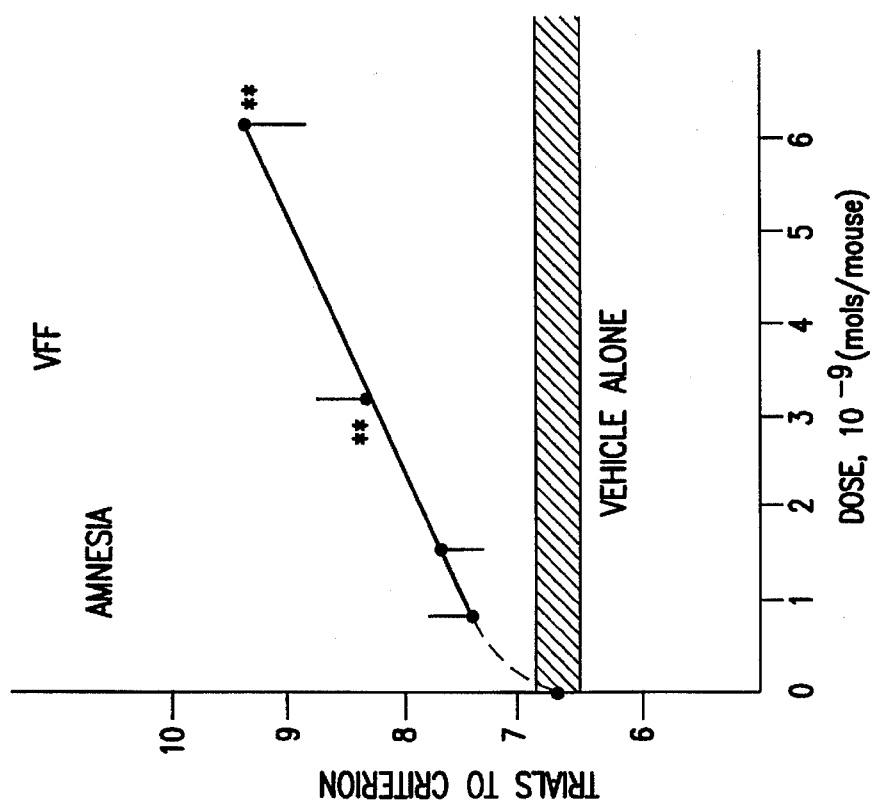
FIGS. 21A and 21B depict memory-enhancing and amnestic effects of Val Phe Phe (SEQ ID NO:5). Experimental conditions in FIG. 21A were adjusted so that vehicle controls had poor retention.
Figure 21A:
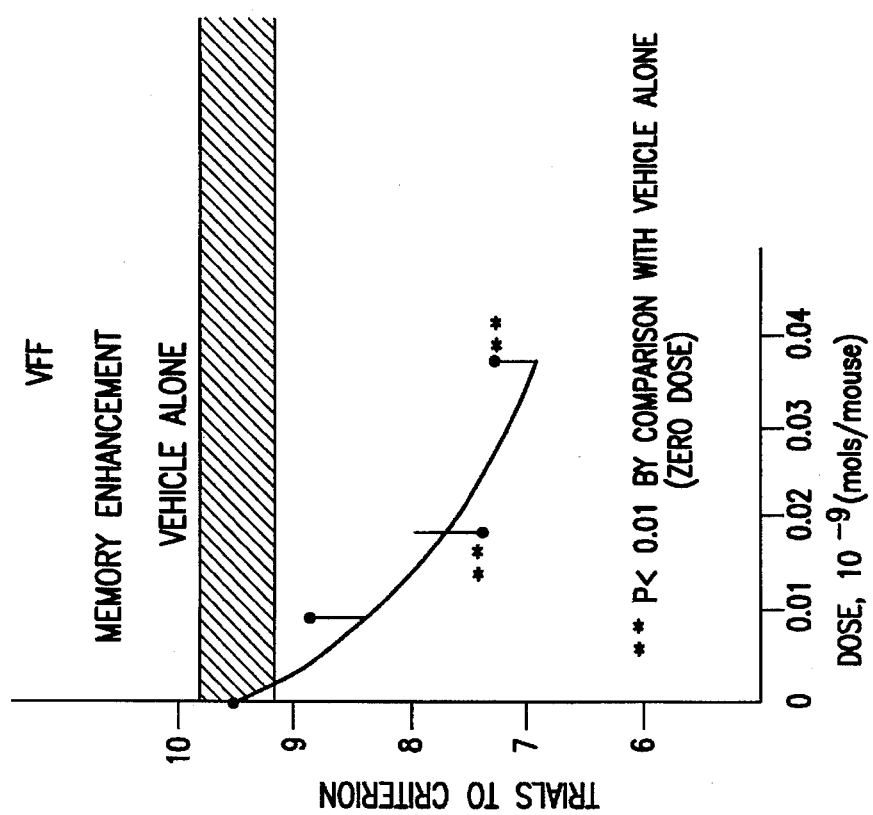

Val Phe Phe is a memory enhancer in weakly trained animals (FIG. 21A) and amnestic when tested in much higher amounts in well-trained animals (FIG. 21B) Statistically significant memory enhancement was first found at $1.9 \times 10^{-11}$ moles/mouse and amnesia first noted at $3 \times 10^{-9}$ moles/mouse. thus, memory enhancement was noted first at a dose less than one-hundredth (0.63%) of that which first produced amnesia. As noted previously in the discussion of the model, Val Phe Phe is proposed to combine with Z at three points of attachment one coulombic and two of them with aromatic groups (Table 1). Comparison of Val Phe Phe to memory enhancement with Val Val Phe and Phe Phe Val Gly showed them to have closely similar potencies (FIG. 5A–C).

Both Val Phe and Phe Val gave closely similar memory-enhancing results (FIGS. 23A and 23B), showing approximately the same potency as Val Phe Phe (Table 1).

All of the above proved to be much weaker than Gln Phe Phe Gly (Table 1). Gln Phe Phe Gly is by far the most potent, producing statistically significant memory enhancement at $10^{-14}$ moles/mouse.

TABLE 1

| | Binding Characteristics on Z of 5 Memory-Enhancing Peptides | | | | | | |
|---|---|---|---|---|---|---|---|
| | Groups on Z to Which the Peptides Bind (See FIGS. 1–3) | | | | | Lowest Concentration For Significant Memory Enhancement | |
| Peptides Tested | 1 H-Bonding | 2 Aromatic | 3 Cationic | 4 Aromatic | 5 Anionic | Moles/Mouse | P Values For Comparison With Vehicle |
| Val Phe Phe | – | + | – | + | + | $1.9 \times 10^{-11}$ | <0.01 |
| Val Phe | – | – | + | + | + | $2 \times 10^{-11}$ | <0.05 |
| Phe Val | – | – | + | + | + | $2 \times 10^{-11}$ | <0.05 |
| Val Val Phe | – | + | – | + | + | $1 \times 10^{-11}$ | <0.05 |
| Phe Phe Val Gly | – | + | + | + | – | $2 \times 10^{-11}$ | <0.05 |
| Gln Phe Phe Gly | + | + | + | + | + | $6 \times 10^{-14}$ | <0.05 |

Additional Peptides and Non-peptidic Substances as Memory Enhancers.

Structure-activity considerations suggest several substances mentioned below that may be effective memory enhancers in the same manner as the effective peptides thus far discovered.

Since by far the most effective memory-enhancing peptide discovered to date by the method developed above is Gln Phe Phe Gly (SEQ ID NO: 12), which touches at all five sites of the postulated memory-related binding sites (Table 1), only those peptides which do likewise are considered below. Computer-assisted fitting procedures and manual work with CPK space-filling molecular models has revealed a series of peptides that fit to Z even more exactly than does Gln Phe Phe Gly. These are discussed below.

Memory-enhancing Peptides Based on Postulated Interaction with All Five Sites on Z.

1. Compounds related to Gln Phe Phe Thr (SEQ ID NO: 17)—C-terminal substitution
    (a) Gln Phe Phe-γ-aminobutyric acid (SEQ ID NO:20)
    (b) Gln Phe Phe-β-alanine (SEQ ID NO:21)
    (c) Gln Phe Phe-δ-aminovaleric acid (SEQ ID NO:22)

Substances (a)–(c) above fit with their C-terminal carboxyl groups closer to cationic site 3 on Z than does Gln Phe Phe Gly and are expected to be more potent memory enhancers than Gln Phe Phe Gly.

2. Compounds related to Gln Phe Phe Thr (SEQ ID NO: 17)—N-terminal substitution
    (a) Lys Phe Phe Gly (SEQ ID NO: 18)
    (b) Arg Phe Phe Gly (SEQ ID NO: 19)
    (c) homoarginyl Phe Phe Gly (SEQ ID NO:23)
    (d) ornithyl Phe Phe Gly (SEQ ID NO:24)

The substitution of Lys and other aliphatic basic amino acids for Gln in Gln Phe Phe Gly is based on the observation that in Lys Leu Phe Phe Val Ala Glu (SEQ ID NO: 9), a potent amnestic (FIG. 1, No. 10), the ε-amino group of Lys can bind to the H-bonding group of site 1 on Z. If this be so, H-bonding via the δ-amino group of ornithine or the guanidino group of Arg or homoarginine also can take place.

3. Compounds related to Gln Phe Phe Gly-substitution for both Gln and Gly with compounds selected from 1a-c and 2a-d while keeping Phe Phe constant, e.g., Arg Phe Phe-δ-aminobutyric acid.

All told, twelve such combinations are possible, in addition to seven listed under items 1 and 2 above.

4. Compounds related to Gln Phe Phe Gly-substitution for Phe-1 and/or Phe-2 by His and/or Tyr in Gln Phe Phe Thr and all of the substances listed in 1a-c and 2a-d.

His and Tyr have properties sufficiently similar to those of Phe so that their affinities for aromatic sites 2 and 4 on Z might be equal to or greater than that of Phe. Arg His Tyr-δ-aminobutyric acid, Lys Tyr Try-β-alanine, etc. This gives a total of 160 compounds that can be tested in this series.

The grand total of 179 substances listed in items 1–4 above does not include many possible variations of the N-terminal or C-terminal groups in the above group of tetrapeptides, such a acetylation of the former or esterification of the latter.

Memory-enhancing Non-peptide Substances Based on Postulated Interaction with All Five Sites on Z.

A long structural search has yielded a new semi-rigid compound (see FIG. 1) that fits Z at all postulated sites at least as well as any of the above peptides.

Numbers refer to sites on Z

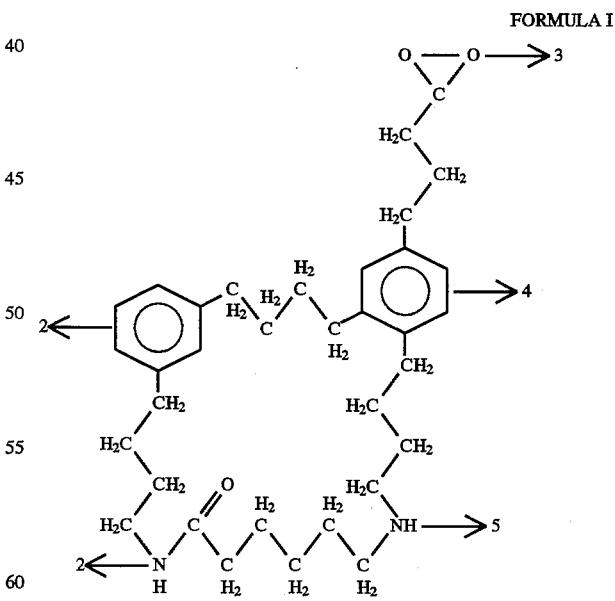

FORMULA I

Providing the ring structure remains intact, many substitutions are possible in the above, e.g., substitutions on the benzene rings, substitution of the latter by imidazole groups, substitution of halogens (fluorine or chlorine) for the carboxypropyl group facing site 3, etc. The compound shown above is only one example of how the Z model can be used in design of potential memory-enhancing substances.

References

1. Flood, J. F., et al. *Proc. Natl. Acad. Sci. USA* 88:3363–3366 (1991)
2. Connolly, M. L., *Science* 221:709–713 (1983)
3. Mayo, S. L., et al. *J. Phys. Chem.* 94:8897–8909 (1990)
4. Ruoslahti, E., *Ann. Rev. Biochem.* 57:375–413 (1988)
5. Kirschner, D. A., et al., *Proc. Natl. Acad. Sci. USA* 84:6953–6957 (1987)
6. Maggio, J. E., et al. *Proc. Natl. Acad. Sci. USA* 89:5462–5466 (1992)
7. Hilbich, C., et al., *J. Mol. Biol.* 228:460–473 (1992)
8. Zagorski, M. G., *Biochemistry* 31:5621–5631 (1992)
9. Jarrett, J. T., *Biochemistry* 32:4693–4697 (1993)
10. Wisniewski, E., et al., *Biochem. Biophys. Res. Commun.* 192:359–365 (1993)
11. Strittmatter, W. J., et al., *Proc. Natl. Acad. Sci. USA* 90:1977–1981 (1993)
12. Flood, J. F., et al., *Peptides* 11:933–938 (1990)
13. Wetzel, W., et al., *Acta biol. med. germ.* 41:647–652 (1982)
14. Schlesinger, K., et al. *Behav. Neural Biol.* 45:230–239 (1986)
15. Hasenohrl, E. U., et al. *Peptides* 11:163–167 (1990)
16. Nagel, J. A., et al. *Peptides* 14:85–95 (1993)
17. Kosik, K., et al., *Neurobiology of Aging* 13:535–625 (Pergamon Press, New York) (1992)
18. Cherkin, A., et al., In: *Cellular Mechanisms of Conditioning and Behavioral Plasticity* (C. D. Woody, D. L. Alkon and J. L. McGaugh, eds.) Plenum Press, New York and London, pp. 343–354 (1988)
19. Drummond, G. I., *Adv. Cyclic Nucleotide Res.* 15:373–494 (1983)

---

I claim:

1. Each of the compounds Gln Phe Phe-γ-aminobutyric acid (SEQ ID NO: 20) Gln Phe Phe-β-alanine (SEQ ID NO: 21) Gln Phe Phe-δ-aminovaleric acid (SEQ ID NO:22) Lys Phe Phe Gly (SEQ ID NO: 18) Arg Phe Phe Gly (SEQ ID NO: 19) Homoarginyl Phe Phe Gly (SEQ ID NO: 23) Ornithyl Phe Phe Gly (SEQ ID NO: 24).

* * * * *

SEQUENCE LISTING ( 1 ) GENERAL INFORMATION:

( i i i ) NUMBER OF SEQUENCES: 24

( 2 ) INFORMATION FOR SEQ ID NO:1:

( i ) SEQUENCE CHARACTERISTICS:
        ( A ) LENGTH: 28 amino acids
        ( B ) TYPE: amino acid
        ( C ) STRANDEDNESS: Not Relevant
        ( D ) TOPOLOGY: Not Relevant ( i i ) MOLECULE TYPE: peptide ( i i i ) HYPOTHETICAL: NO ( v ) FRAGMENT TYPE: N-terminal ( x i ) SEQUENCE DESCRIPTION: SEQ ID NO:1:

Asp Ala Glu Phe Arg His Asp Ser Gly Tyr Gln Val His His Gln Lys
1               5                   10                  15
Leu Val Phe Phe Ala Glu Asp Val Gly Ser Asn Lys
            20                  25

( 2 ) INFORMATION FOR SEQ ID NO:2:

( i ) SEQUENCE CHARACTERISTICS:
        ( A ) LENGTH: 17 amino acids
        ( B ) TYPE: amino acid
        ( C ) STRANDEDNESS: Not Relevant
        ( D ) TOPOLOGY: Not Relevant ( i i ) MOLECULE TYPE: peptide ( i i i ) HYPOTHETICAL: NO ( v ) FRAGMENT TYPE: internal ( x i ) SEQUENCE DESCRIPTION: SEQ ID NO:2:

Val His His Gln Lys Leu Val Phe Phe Ala Glu Asp Val Gly Ser Asn
1               5                   10                  15
Lys ( 2 ) INFORMATION FOR SEQ ID NO:3:

( i ) SEQUENCE CHARACTERISTICS:
        ( A ) LENGTH: 11 amino acids
        ( B ) TYPE: amino acid
        ( C ) STRANDEDNESS: Not Relevant
        ( D ) TOPOLOGY: Not Relevant ( i i ) MOLECULE TYPE: peptide ( i i i ) HYPOTHETICAL: NO ( v ) FRAGMENT TYPE: internal ( x i ) SEQUENCE DESCRIPTION: SEQ ID NO:3:

```
Val  Phe  Phe  Ala  Glu  Asp  Val  Gly  Ser  Asn  Lys
 1             5                             10
```

( 2 ) INFORMATION FOR SEQ ID NO:4:

( i ) SEQUENCE CHARACTERISTICS:
        ( A ) LENGTH: 9 amino acids
        ( B ) TYPE: amino acid
        ( C ) STRANDEDNESS: Not Relevant
        ( D ) TOPOLOGY: Not Relevant ( i i ) MOLECULE TYPE: peptide ( i i i ) HYPOTHETICAL: NO ( v ) FRAGMENT TYPE: internal ( x i ) SEQUENCE DESCRIPTION: SEQ ID NO:4:

```
Val  His  His  Gln  Lys  Leu  Val  Phe  Phe
 1             5
```

( 2 ) INFORMATION FOR SEQ ID NO:5:

( i ) SEQUENCE CHARACTERISTICS:
        ( A ) LENGTH: 3 amino acids
        ( B ) TYPE: amino acid
        ( C ) STRANDEDNESS: Not Relevant
        ( D ) TOPOLOGY: Not Relevant ( i i ) MOLECULE TYPE: peptide ( i i i ) HYPOTHETICAL: NO ( v ) FRAGMENT TYPE: internal ( x i ) SEQUENCE DESCRIPTION: SEQ ID NO:5:

```
Val  Phe  Phe
 1
```

( 2 ) INFORMATION FOR SEQ ID NO:6:

( i ) SEQUENCE CHARACTERISTICS:
        ( A ) LENGTH: 11 amino acids
        ( B ) TYPE: amino acid
        ( C ) STRANDEDNESS: Not Relevant
        ( D ) TOPOLOGY: Not Relevant ( i i ) MOLECULE TYPE: peptide ( i i i ) HYPOTHETICAL: NO ( v ) FRAGMENT TYPE: N-terminal ( x i ) SEQUENCE DESCRIPTION: SEQ ID NO:6:

```
Asp  Ala  Glu  Phe  Arg  His  Asp  Ser  Gly  Tyr  Gln
 1             5                             10
```

( 2 ) INFORMATION FOR SEQ ID NO:7:

( i ) SEQUENCE CHARACTERISTICS:
        ( A ) LENGTH: 4 amino acids
        ( B ) TYPE: amino acid
        ( C ) STRANDEDNESS: Not Relevant
        ( D ) TOPOLOGY: Not Relevant ( i i ) MOLECULE TYPE: peptide ( i i i ) HYPOTHETICAL: YES ( v ) FRAGMENT TYPE: internal ( x i ) SEQUENCE DESCRIPTION: SEQ ID NO:7:

Ala Val Phe Thr
    1

( 2 ) INFORMATION FOR SEQ ID NO:8:

( i ) SEQUENCE CHARACTERISTICS:
        ( A ) LENGTH: 3 amino acids
        ( B ) TYPE: amino acid
        ( C ) STRANDEDNESS: Not Relevant
        ( D ) TOPOLOGY: Not Relevant ( i i ) MOLECULE TYPE: peptide ( i i i ) HYPOTHETICAL: YES ( v ) FRAGMENT TYPE: internal ( x i ) SEQUENCE DESCRIPTION: SEQ ID NO:8:

Val Ile Pro
    1

( 2 ) INFORMATION FOR SEQ ID NO:9:

( i ) SEQUENCE CHARACTERISTICS:
        ( A ) LENGTH: 7 amino acids
        ( B ) TYPE: amino acid
        ( C ) STRANDEDNESS: Not Relevant
        ( D ) TOPOLOGY: Not Relevant ( i i ) MOLECULE TYPE: peptide ( i i i ) HYPOTHETICAL: YES ( v ) FRAGMENT TYPE: internal ( x i ) SEQUENCE DESCRIPTION: SEQ ID NO:9:

Lys Leu Phe Phe Val Ala Glu
    1                    5

( 2 ) INFORMATION FOR SEQ ID NO:10:

( i ) SEQUENCE CHARACTERISTICS:
        ( A ) LENGTH: 6 amino acids
        ( B ) TYPE: amino acid
        ( C ) STRANDEDNESS: Not Relevant
        ( D ) TOPOLOGY: Not Relevant ( i i ) MOLECULE TYPE: peptide ( i i i ) HYPOTHETICAL: YES ( v ) FRAGMENT TYPE: internal ( x i ) SEQUENCE DESCRIPTION: SEQ ID NO:10:

Val Phe Phe Val Val Phe
    1                    5

( 2 ) INFORMATION FOR SEQ ID NO:11:

( i ) SEQUENCE CHARACTERISTICS:
        ( A ) LENGTH: 4 amino acids
        ( B ) TYPE: amino acid
        ( C ) STRANDEDNESS: Not Relevant
        ( D ) TOPOLOGY: Not Relevant ( i i ) MOLECULE TYPE: peptide ( i i i ) HYPOTHETICAL: YES ( v ) FRAGMENT TYPE: internal ( x i ) SEQUENCE DESCRIPTION: SEQ ID NO:11:

Phe  Phe  Val  Gly
    1

( 2 ) INFORMATION FOR SEQ ID NO:12:

( i ) SEQUENCE CHARACTERISTICS:
        ( A ) LENGTH: 4 amino acids
        ( B ) TYPE: amino acid
        ( C ) STRANDEDNESS: Not Relevant
        ( D ) TOPOLOGY: Not Relevant ( i i ) MOLECULE TYPE: peptide ( i i i ) HYPOTHETICAL: NO ( v ) FRAGMENT TYPE: internal ( x i ) SEQUENCE DESCRIPTION: SEQ ID NO:12:

Gln  Phe  Phe  Gly
    1

( 2 ) INFORMATION FOR SEQ ID NO:13:

( i ) SEQUENCE CHARACTERISTICS:
        ( A ) LENGTH: 7 amino acids
        ( B ) TYPE: amino acid
        ( C ) STRANDEDNESS: Not Relevant
        ( D ) TOPOLOGY: Not Relevant ( i i ) MOLECULE TYPE: peptide ( i i i ) HYPOTHETICAL: NO ( v ) FRAGMENT TYPE: internal ( x i ) SEQUENCE DESCRIPTION: SEQ ID NO:13:

Lys  Leu  Val  Phe  Phe  Ala  Glu
    1                        5

( 2 ) INFORMATION FOR SEQ ID NO:14:

( i ) SEQUENCE CHARACTERISTICS:
        ( A ) LENGTH: 3 amino acids
        ( B ) TYPE: amino acid
        ( C ) STRANDEDNESS: Not Relevant
        ( D ) TOPOLOGY: Not Relevant ( i i ) MOLECULE TYPE: peptide ( i i i ) HYPOTHETICAL: NO ( v ) FRAGMENT TYPE: internal ( x i ) SEQUENCE DESCRIPTION: SEQ ID NO:14:

Arg  Gly  Asp
    1

( 2 ) INFORMATION FOR SEQ ID NO:15:

( i ) SEQUENCE CHARACTERISTICS:
        ( A ) LENGTH: 27 amino acids
        ( B ) TYPE: amino acid
        ( C ) STRANDEDNESS: Not Relevant
        ( D ) TOPOLOGY: Not Relevant ( i i ) MOLECULE TYPE: peptide ( i i i ) HYPOTHETICAL: NO ( v ) FRAGMENT TYPE: N-terminal ( x i ) SEQUENCE DESCRIPTION: SEQ ID NO:15:

```
His  Ser  Asp  Ala  Val  Phe  Thr  Asp  Asn  Tyr  Thr  Arg  Leu  Lys  Gln  Met
 1              5                        10                            15

Ala  Val  Lys  Lys  Tyr  Leu  Asn  Ser  Ile  Leu  Asn
               20                        25
```

( 2 ) INFORMATION FOR SEQ ID NO:16:

( i ) SEQUENCE CHARACTERISTICS:
        ( A ) LENGTH: 12 amino acids
        ( B ) TYPE: amino acid
        ( C ) STRANDEDNESS: Not Relevant
        ( D ) TOPOLOGY: Not Relevant ( i i ) MOLECULE TYPE: peptide ( i i i ) HYPOTHETICAL: NO ( v ) FRAGMENT TYPE: N-terminal ( x i ) SEQUENCE DESCRIPTION: SEQ ID NO:16:

```
Pro  Arg  Pro  Gly  Pro  Gln  Gln  Phe  Phe  Gly  Leu  Met
 1              5                        10
```

( 2 ) INFORMATION FOR SEQ ID NO:17:

( i ) SEQUENCE CHARACTERISTICS:
        ( A ) LENGTH: 4 amino acids
        ( B ) TYPE: amino acid
        ( C ) STRANDEDNESS: Not Relevant
        ( D ) TOPOLOGY: Not Relevant ( i i ) MOLECULE TYPE: peptide ( i i i ) HYPOTHETICAL: YES ( v ) FRAGMENT TYPE: internal ( x i ) SEQUENCE DESCRIPTION: SEQ ID NO:17:

```
Gln  Phe  Phe  Thr
 1
```

( 2 ) INFORMATION FOR SEQ ID NO:18:

( i ) SEQUENCE CHARACTERISTICS:
        ( A ) LENGTH: 4 amino acids
        ( B ) TYPE: amino acid
        ( C ) STRANDEDNESS: Not Relevant
        ( D ) TOPOLOGY: Not Relevant ( i i ) MOLECULE TYPE: peptide ( i i i ) HYPOTHETICAL: YES ( v ) FRAGMENT TYPE: internal ( x i ) SEQUENCE DESCRIPTION: SEQ ID NO:18:

```
    Lys  Phe  Phe  Gly
    1
```

(2) INFORMATION FOR SEQ ID NO:19:

(i) SEQUENCE CHARACTERISTICS:
        (A) LENGTH: 4 amino acids
        (B) TYPE: amino acid
        (C) STRANDEDNESS: Not Relevant
        (D) TOPOLOGY: Not Relevant (ii) MOLECULE TYPE: peptide (iii) HYPOTHETICAL: YES (v) FRAGMENT TYPE: internal (xi) SEQUENCE DESCRIPTION: SEQ ID NO:19:

```
    Arg  Phe  Phe  Gly
    1
```

(2) INFORMATION FOR SEQ ID NO:20:

(i) SEQUENCE CHARACTERISTICS:
        (A) LENGTH: 4 amino acids
        (B) TYPE: amino acid
        (C) STRANDEDNESS: Not Relevant
        (D) TOPOLOGY: Not Relevant (ii) MOLECULE TYPE: peptide (iii) HYPOTHETICAL: YES (v) FRAGMENT TYPE: internal (ix) FEATURE:
        (A) NAME/KEY: Modified-site
        (B) LOCATION: 4
        (D) OTHER INFORMATION: gamma aminobutyric acid (xi) SEQUENCE DESCRIPTION: SEQ ID NO:20:

```
    Gln  Phe  Phe  Xaa
    1
```

(2) INFORMATION FOR SEQ ID NO:21:

(i) SEQUENCE CHARACTERISTICS:
        (A) LENGTH: 4 amino acids
        (B) TYPE: amino acid
        (C) STRANDEDNESS: Not Relevant
        (D) TOPOLOGY: Not Relevant (ii) MOLECULE TYPE: peptide (iii) HYPOTHETICAL: YES (v) FRAGMENT TYPE: internal (ix) FEATURE:
        (A) NAME/KEY: Modified-site
        (B) LOCATION: 4
        (D) OTHER INFORMATION: beta alanine (xi) SEQUENCE DESCRIPTION: SEQ ID NO:21:

```
    Gln  Phe  Phe  Xaa
    1
```

(2) INFORMATION FOR SEQ ID NO:22:

(i) SEQUENCE CHARACTERISTICS:
        (A) LENGTH: 4 amino acids
        (B) TYPE: amino acid
        (C) STRANDEDNESS: Not Relevant

```
            ( D ) TOPOLOGY: Not Relevant ( i i ) MOLECULE TYPE: peptide ( i i i ) HYPOTHETICAL: YES ( v ) FRAGMENT TYPE: internal ( i x ) FEATURE:
            ( A ) NAME/KEY: Modified-site
            ( B ) LOCATION: 4
            ( D ) OTHER INFORMATION: delta aminovaleric acid ( x i ) SEQUENCE DESCRIPTION: SEQ ID NO:22:

Gln  Phe  Phe  Xaa
    1

( 2 ) INFORMATION FOR SEQ ID NO:23:

( i ) SEQUENCE CHARACTERISTICS:
            ( A ) LENGTH: 4 amino acids
            ( B ) TYPE: amino acid
            ( C ) STRANDEDNESS: Not Relevant
            ( D ) TOPOLOGY: Not Relevant ( i i ) MOLECULE TYPE: peptide ( i i i ) HYPOTHETICAL: YES ( v ) FRAGMENT TYPE: internal ( i x ) FEATURE:
            ( A ) NAME/KEY: Modified-site
            ( B ) LOCATION: 1
            ( D ) OTHER INFORMATION: homoarginine ( x i ) SEQUENCE DESCRIPTION: SEQ ID NO:23:

Xaa  Phe  Phe  Gly
    1

( 2 ) INFORMATION FOR SEQ ID NO:24:

( i ) SEQUENCE CHARACTERISTICS:
            ( A ) LENGTH: 4 amino acids
            ( B ) TYPE: amino acid
            ( C ) STRANDEDNESS: Not Relevant
            ( D ) TOPOLOGY: Not Relevant ( i i ) MOLECULE TYPE: peptide ( i i i ) HYPOTHETICAL: YES ( v ) FRAGMENT TYPE: internal ( i x ) FEATURE:
            ( A ) NAME/KEY: Modified-site
            ( B ) LOCATION: 1
            ( D ) OTHER INFORMATION: ornithine ( x i ) SEQUENCE DESCRIPTION: SEQ ID NO:24:

Xaa  Phe  Phe  Gly
    1
```